US010538518B2

(12) United States Patent
Zhu et al.

(10) Patent No.: US 10,538,518 B2
(45) Date of Patent: Jan. 21, 2020

(54) PROCESSES FOR PREPARING AN FGFR INHIBITOR

(71) Applicant: Principia Biopharma, Inc., South San Francisco, CA (US)

(72) Inventors: Jiang Zhu, San Ramon, CA (US); Mohammad Masjedizadeh, San Jose, CA (US)

(73) Assignee: Principia Biopharma, Inc., South San Francisco, CA (US)

( * ) Notice: Subject to any disclaimer, the term of this patent is extended or adjusted under 35 U.S.C. 154(b) by 0 days.

(21) Appl. No.: 15/748,212

(22) PCT Filed: Aug. 10, 2016

(86) PCT No.: PCT/US2016/046304
§ 371 (c)(1),
(2) Date: Jan. 29, 2018

(87) PCT Pub. No.: WO2017/027567
PCT Pub. Date: Feb. 16, 2017

(65) Prior Publication Data
US 2018/0215756 A1   Aug. 2, 2018

Related U.S. Application Data

(60) Provisional application No. 62/203,498, filed on Aug. 11, 2015.

(51) Int. Cl.
| C07D 471/04 | (2006.01) |
| A61P 35/00 | (2006.01) |
| C07B 35/02 | (2006.01) |
| C07B 35/06 | (2006.01) |
| C07B 39/00 | (2006.01) |
| C07B 43/04 | (2006.01) |
| C07B 43/06 | (2006.01) |
| C07B 45/04 | (2006.01) |

(52) U.S. Cl.
CPC ............ *C07D 471/04* (2013.01); *A61P 35/00* (2018.01); *C07B 35/02* (2013.01); *C07B 35/06* (2013.01); *C07B 39/00* (2013.01); *C07B 43/04* (2013.01); *C07B 43/06* (2013.01); *C07B 45/04* (2013.01); *C07B 2200/13* (2013.01)

(58) Field of Classification Search
CPC .................................................. C07D 471/04
See application file for complete search history.

(56) References Cited

U.S. PATENT DOCUMENTS 9,567,334 B2 * 2/2017 Verner ................. C07D 471/04

FOREIGN PATENT DOCUMENTS

| EP | 2230243 | 9/2010 |
| WO | 2014011900 | 1/2014 |
| WO | 2014182829 | 11/2014 |
| WO | 2015120049 | 8/2015 |

OTHER PUBLICATIONS

Patent Cooperation Treaty, International Search Report for PCT/US2016/046304, dated Oct. 7, 2016, 7 pages Oct. 7, 2016.
Biancalani et al., Further studies on Arylpiperazinyl Alkyl Pyridazinones: Discovery of an exceptionally potent, orally active, antinociceptive agent in thermally induced pain, J. Med. Chem., 2009, 52: 7397-7409 2009.
Yang et al., Application of a C—C Bond-Forming Conjugate Addition Reaction in Asymmetric Dearomatization of Beta-Naphthols, Angew. Chem. Ind. Ed., 2015, 54: 9523-9527 2015.
Aitken et al., Flash vacuum pyrolysis over magnesium. Part 1. Pyrolysis of benzylic,other ary/alkyl and aliphatic halides, J. Chem. Soc. Perkin Trans., 2002, 1: 402-415 2002.

* cited by examiner

*Primary Examiner* — Emily A Bernhardt
(74) *Attorney, Agent, or Firm* — Bryan Cave Leighton Paisner LLP

(57) ABSTRACT

To an appropriate reactor equipped with mechanical stirrer was charged acetic acid (12 L), tert-butyl 4-(3-(6-(3,5-dimethoxyphenyl)-2-(methylthio)-7-oxopyrido[2,3-d]pyrimidin-8(7H)-yl)propyl)piperazine-1-carboxylate (2000 g) and triethylamine (639 g, 2.3 eq.). Internal temperature was adjusted to approximately 20° C. and N-chlorosuccinimide (1651 g, 4.5 eq.) was added at 20-30° C. Reaction was stirred for 2 hours. Ethyl acetate (30 L) was added. 5% aqueous NaCl solution (20 L) was added. The organic layer was separated and the aqueous layer was extracted with EtOAc. The combined organic layers were washed with 30% aqueous potassium carbonate solution (14 L). The organic layer was concentrated to ~12 L and used for next step directly.

7 Claims, 16 Drawing Sheets

| INDEX | FREQUENCY | PPM | HEIGHT |
|---|---|---|---|
| 1 | 3069.1 | 7.676 | 8.0 |
| 2 | 2790.2 | 6.979 | 7.1 |
| 3 | 1580.9 | 3.954 | 40.8 |
| 4 | 1326.0 | 3.317 | 135.3 |
| 5 | 1169.2 | 2.924 | 7.5 |
| 6 | 1164.4 | 2.912 | 7.5 |
| 7 | 1003.7 | 2.510 | 7.4 |
| 8 | 1001.9 | 2.506 | 16.2 |
| 9 | 1000.0 | 2.501 | 22.9 |
| 10 | 998.3 | 2.497 | 16.9 |
| 11 | 996.5 | 2.492 | 8.1 |
| 12 | 919.4 | 2.300 | 4.0 |
| 13 | 0.0 | 0.000 | 13.7 |

FIG. 3B

| Elap Time min | Weight mg | Weight % chg | Samp Temp deg C | Samp RH % |
|---|---|---|---|---|
| 0.1 | 14.144 | 0.000 | 25.29 | 0.84 |
| 11.1 | 14.143 | -0.011 | 25.37 | 4.96 |
| 34.1 | 14.144 | 0.000 | 25.36 | 14.51 |
| 47.6 | 14.148 | 0.024 | 25.36 | 24.82 |
| 62.7 | 14.152 | 0.056 | 25.37 | 34.93 |
| 83.7 | 14.159 | 0.100 | 25.37 | 45.00 |
| 104.2 | 14.167 | 0.159 | 25.37 | 54.86 |
| 126.2 | 14.174 | 0.207 | 25.37 | 64.91 |
| 144.7 | 14.178 | 0.238 | 25.37 | 75.02 |
| 163.2 | 14.183 | 0.271 | 25.37 | 85.09 |
| 182.2 | 14.188 | 0.309 | 25.36 | 94.79 |
| 195.8 | 14.184 | 0.282 | 25.36 | 85.15 |
| 209.3 | 14.180 | 0.251 | 25.36 | 75.26 |
| 226.3 | 14.175 | 0.215 | 25.36 | 65.00 |
| 245.8 | 14.169 | 0.175 | 25.34 | 54.94 |
| 267.8 | 14.160 | 0.107 | 25.36 | 45.03 |
| 288.8 | 14.152 | 0.056 | 25.36 | 35.06 |
| 305.9 | 14.147 | 0.021 | 25.36 | 25.09 |
| 328.9 | 14.143 | -0.009 | 25.37 | 15.16 |
| 342.4 | 14.140 | -0.029 | 25.36 | 5.34 |

PROCESSES FOR PREPARING AN FGFR INHIBITOR

This application is a national phase application based on international application number PCT/US2016/046304 filed Aug. 10, 2016 which claims the benefit of priority of U.S. Provisional Application No. 62/203,498 filed Aug. 11, 2015, the contents of each of which are incorporated by reference herein in their entirety.

FIELD

Disclosed herein are processes for preparing 8-(3-(4-acryloylpiperazin-1-yl)propyl)-6-(2,6-dichloro-3,5-dimethoxyphenyl)-2-(methylamino)pyrido[2,3-d]pyrimidin-7 (8H)-one (hereinafter Compound (I) having the structure:

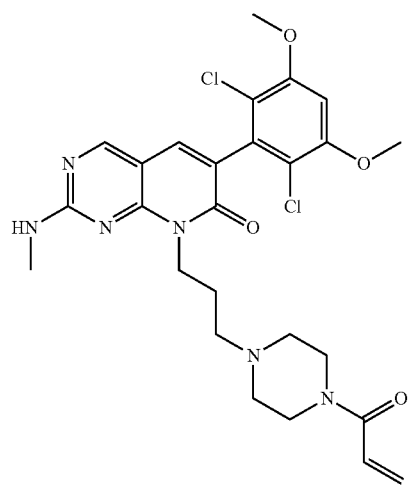

(I)

or a salt of compound (I). Compound (I) is an FGFR inhibitor and hence useful for treating diseases mediated by aberrant activity of FGFR such as cancer, including but not limited to, breast cancer, multiple myeloma, bladder cancer, non-muscle invasive bladder cancer, endometrial cancer, gastric cancer, cervical cancer, rhabdomyosarcoma, lung cancer, squamous non-small cell lung cancer, cholangiocarcinoma, urothelial cancer, renal cell carcinoma, ovarian cancer, esophageal cancer, melanoma, colon cancer, liver cancer, hepatocellular carcinoma, head and neck squamous cell carcinoma, cholangiocarcinoma, glioma, cholangiocarcinoma, 8,11 myeloproliferative syndrome, myeloproliferative disorders involving FGFR translocations/fusions, alveolar rhabdomyosarcoma, malignant rhabdoid tumors, glioblastoma, muscle invasive bladder or renal cancer and prostate cancers.

Compound (I) is disclosed in Example 6 of the PCT Application No. PCT/US15/14460 filed on Feb. 4, 2015. Provided are processes that are conducive to preparing large scale synthesis of Compound (I).

SUMMARY

According to one aspect, a process is provided for preparing a Compound (I):

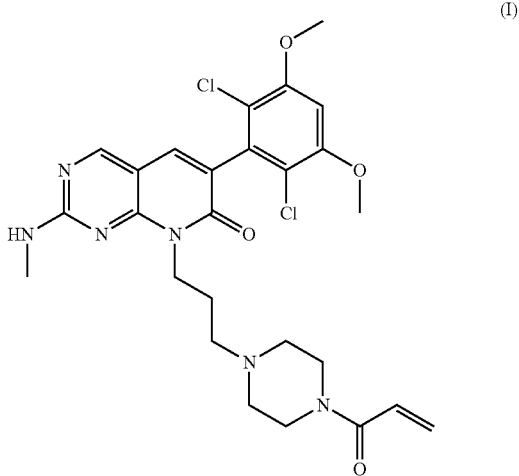 [SMILES: C=CC(=O)N1CCN(CCCn2c(=O)c(-c3c(Cl)c(OC)cc(OC)c3Cl)cc3cnc(NC)nc32)CC1]

(I)

including:
(A) treating compound of formula (a) (where X is a leaving group under elimination reaction conditions) with a base

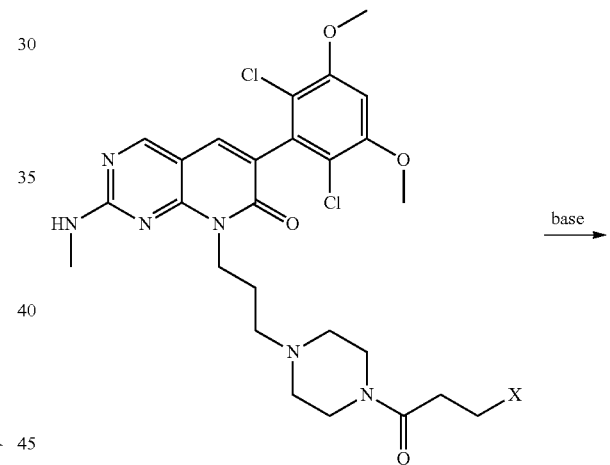

(a)

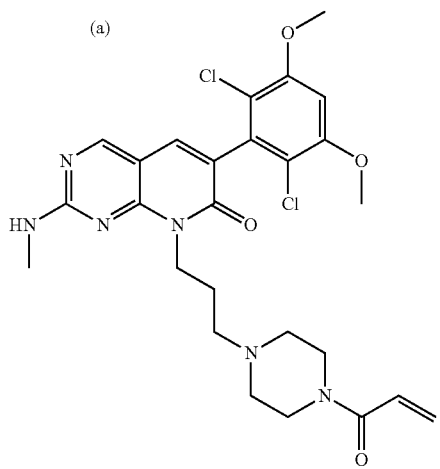

(I)

to provide Compound (I); or (B) reducing the acetylene bond in compound (b)
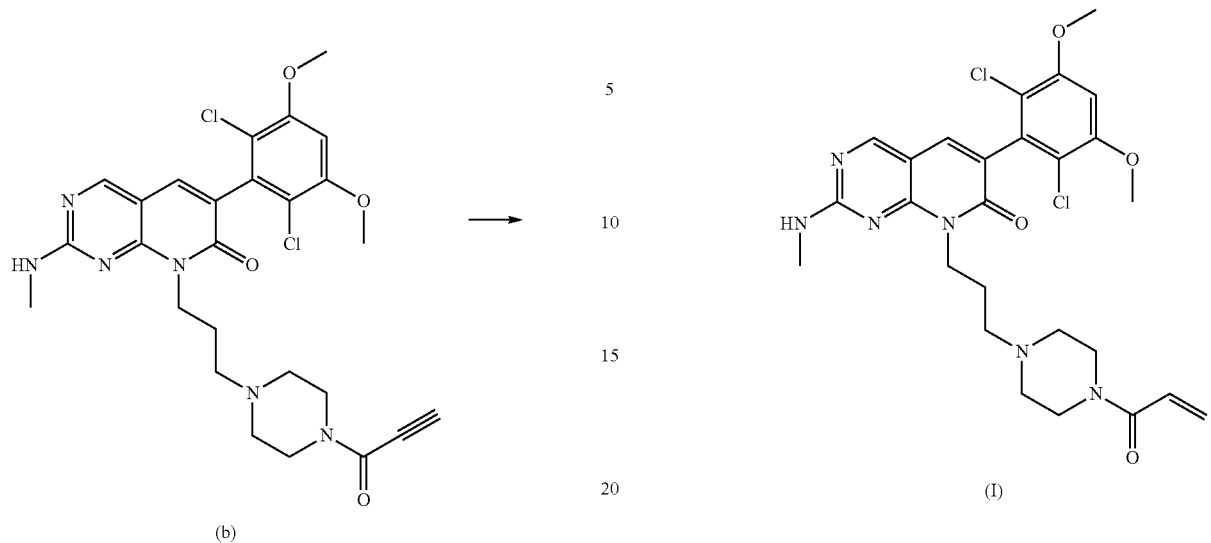
(b)
to provide Compound (I); or
(C) treating a compound of formula (c) with a reducing agent
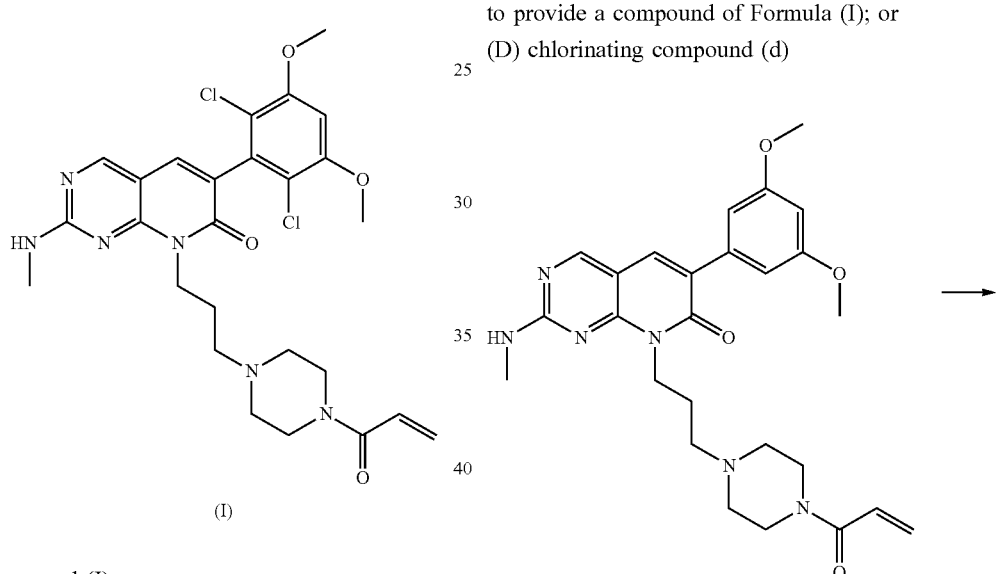
(c)
-continued
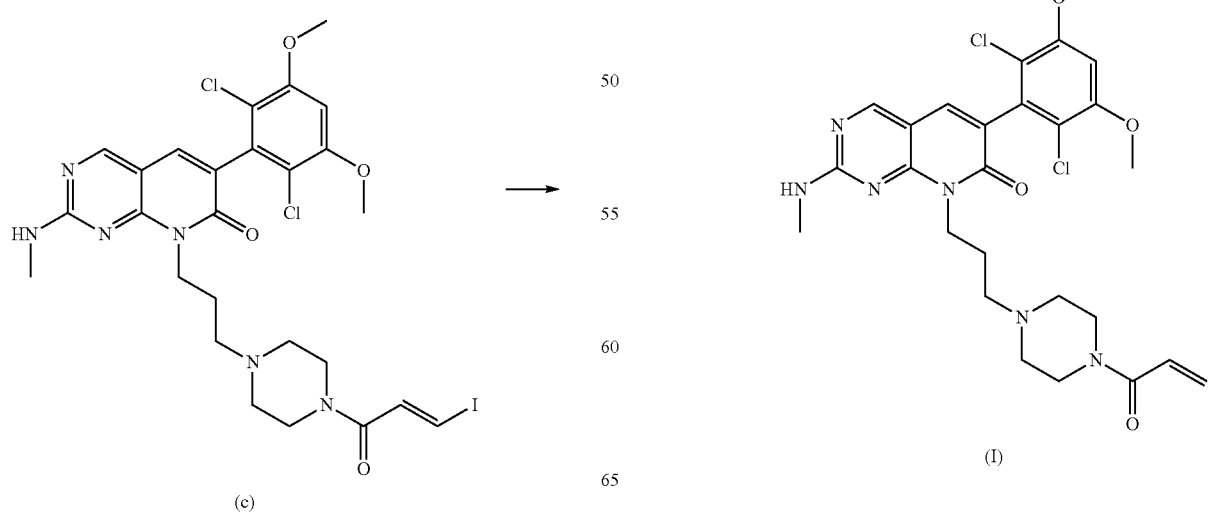
(I)
to provide a compound of Formula (I); or
(D) chlorinating compound (d)
(d)
to provide Compound (I); and (E) optionally converting Compound (I) obtained from reaction (A), (B), (C), or (D) above to an acid addition salt; or (F) optionally converting Compound (I) obtained from reaction (A), (B), (C), or (D) above to the free base.

According to another aspect, a process is provided for preparing a compound (1):

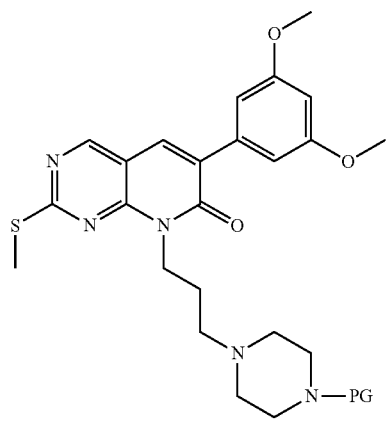

where PG is a amino protecting group (preferably tert-butoxycarbonyl or benzyloxycarbonyl, more preferably tert-butoxycarbonyl); including:

(G) reacting a compound of formula (e):

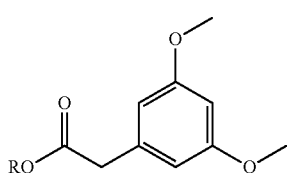

where R is alkyl (preferably methyl or ethyl); with a compound of formula (f):

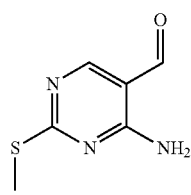

and (H) treating a compound of formula (g) formed in situ

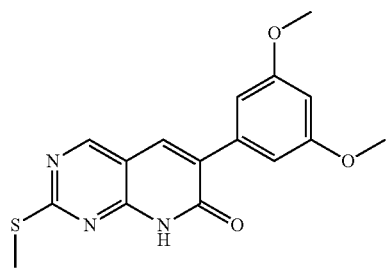

from reaction of compound (e) and (f) with a compound of formula (h) or a salt thereof

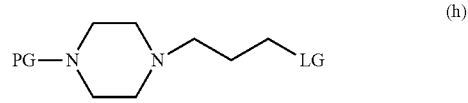

where PG is an amino protecting group (preferably tert-butoxycarbonyl or benzyloxycarbonyl, more preferably tert-butoxycarbonyl) and LG is a leaving group under alkylating reaction conditions (such as halo, tosylate, mesylate, triflate, and the like, preferably mesylate) to provide a compound of formula (1).

According to another aspect, a process is provided for preparing a compound of formula (d) including reacting a compound of formula (6) with a compound of formula (iii) where LG is a group under acylating reaction conditions

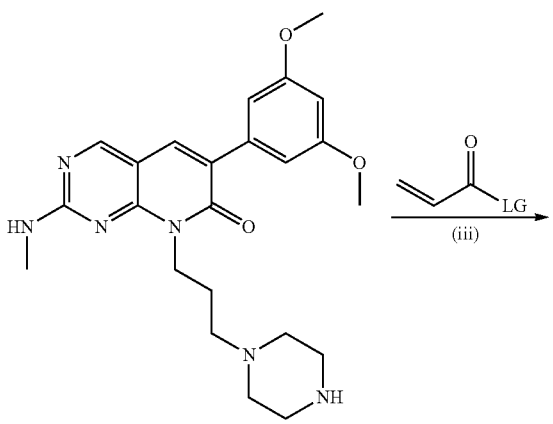

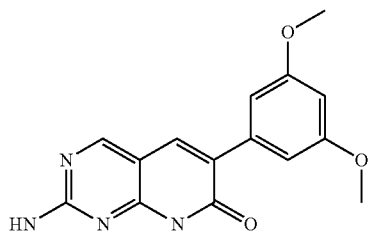

to give a compound of formula (d); or reacting a compound of formula (6) with an propenoic acid under amide bond formation reaction conditions:

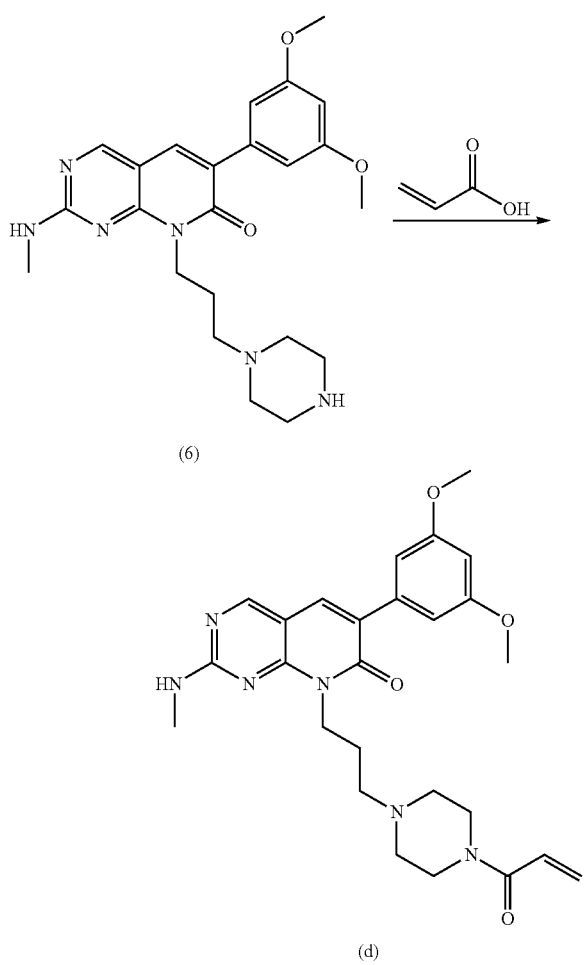

to give a compound of formula (d).

According to yet another aspect, an intermediate of formula (6) is provided:

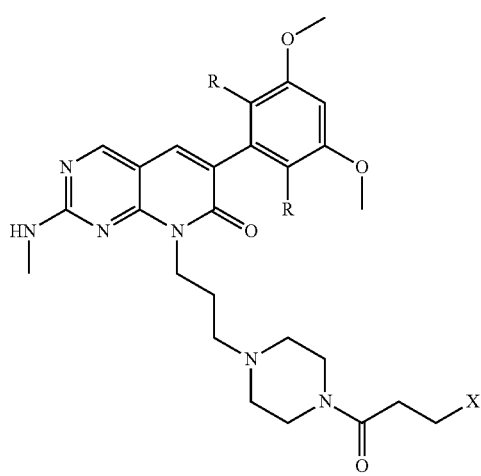

where:
both R are either hydrogen or chloro; and
X is halo, phosphate, tosylate, or mesylate; or
a salt thereof.

According to yet another aspect, crystalline 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided. In particular, according to one aspect, a crystalline free base is provided of a compound of formula:

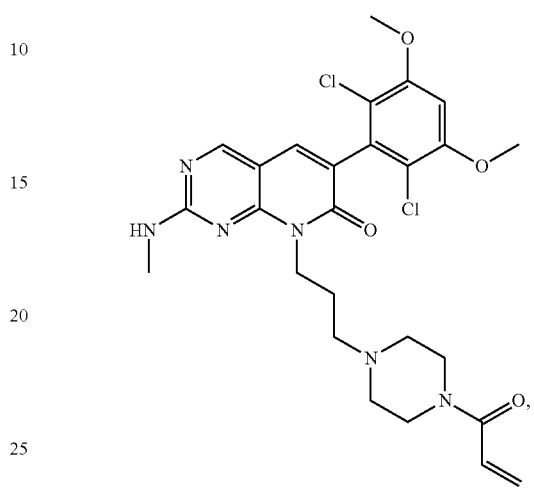

characterized by an X-ray powder diffraction (XRPD) pattern comprising a characteristic peak at about 22° 2Θ (Form 1).

According to another aspect, a crystalline free base of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided in a hydrate form (Form 3). The hydrate form (Form 3) may be characterized by an X-ray powder diffraction (XRPD) pattern comprising a characteristic peak at about 6° 2Θ.

According to another aspect, a crystalline free base of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided in a solvate form (Forms 7, 10 and/or 14). The solvate form (Forms 7, 10 and/or 14) may be characterized by an X-ray powder diffraction (XRPD) pattern comprising a characteristic peak at about 14° 2Θ.

According to another aspect, an amorphous form of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided. The amorphous form may be characterized by an X-ray powder diffraction (XRPD) pattern comprising a characteristic disordered halo at about 23° 2Θ.

According to another aspect, a crystalline hydrochloride salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided. The hydrochloride salt may be characterized by an X-ray powder diffraction (XRPD) pattern comprising a characteristic peak at about 11° 2Θ.

According to yet aspect, a crystalline maleate salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one (Compound I) is provided. The maleate salt may be characterized by an X-ray powder diffraction (XRPD) pattern comprising a characteristic peak at about 22.5° 2Θ.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein.

FIG. 3B shows proton NMR peaks of Form 1 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

DETAILED DESCRIPTION OF THE INVENTION

Figure 1A:
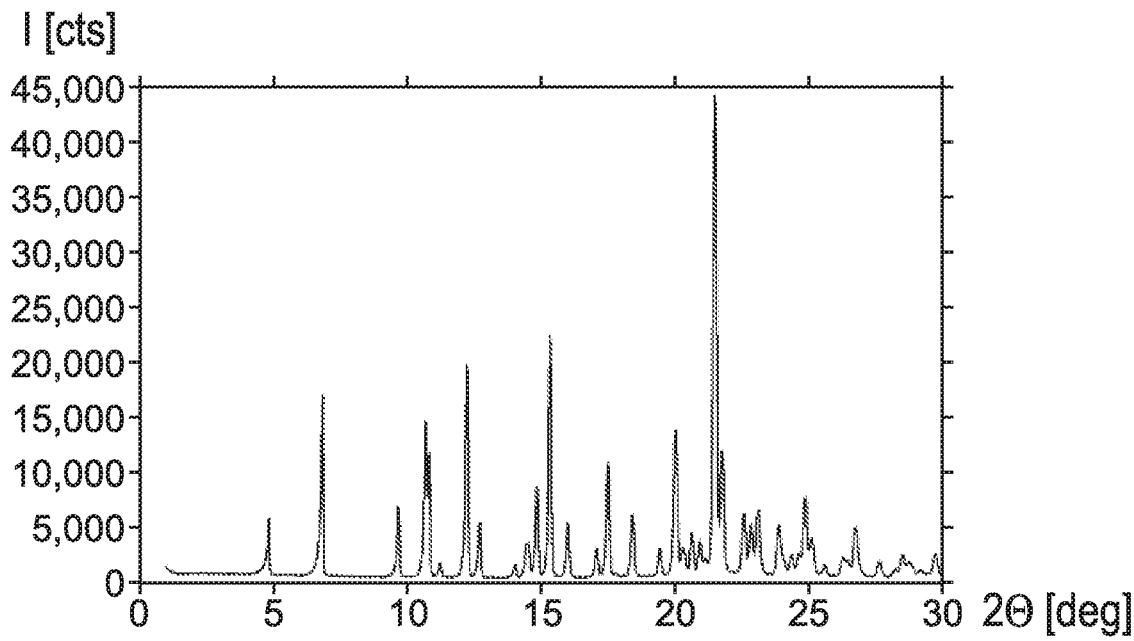
FIGS. 1A-1C show the XRPD spectra of Form 1 of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

In a first aspect, disclosed is a process of preparing a Compound (I):

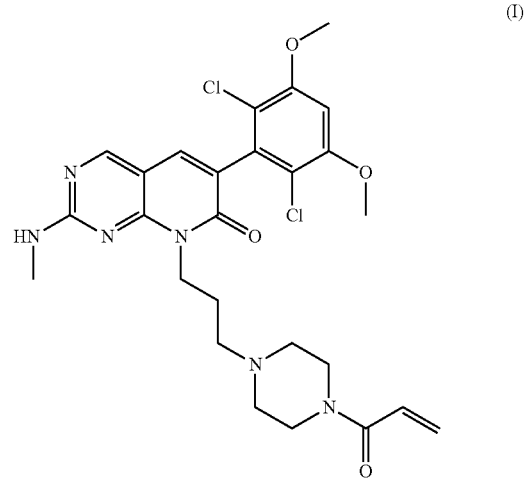 [SMILES: C=CC(=O)N1CCN(CCCn2c(=O)c(-c3c(Cl)c(OC)cc(OC)c3Cl)cc3cnc(NC)nc32)CC1]

(I)

comprising:

(A) treating compound of formula (a) (where X is a leaving group under elimination reaction conditions) with a base

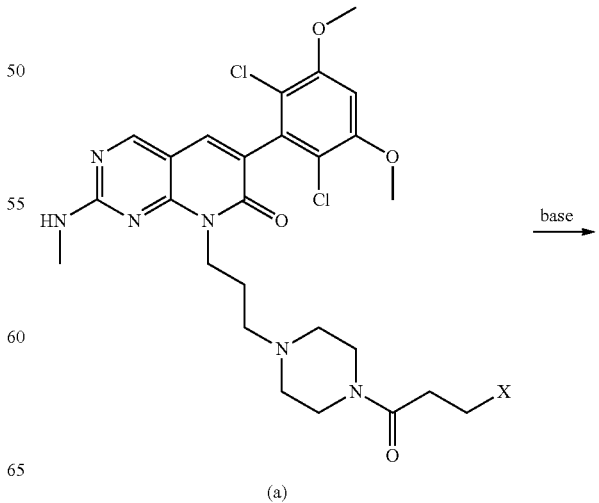

(a)

-continued
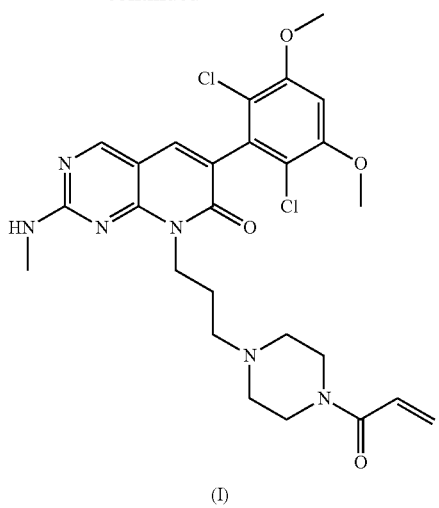
(I)
to provide Compound (I); or
(B) reducing the acetylene bond in compound (b)
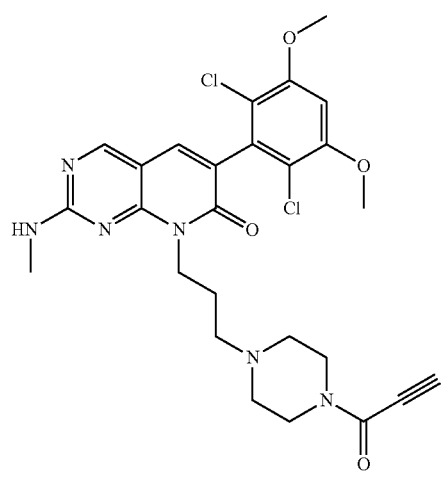
(b)
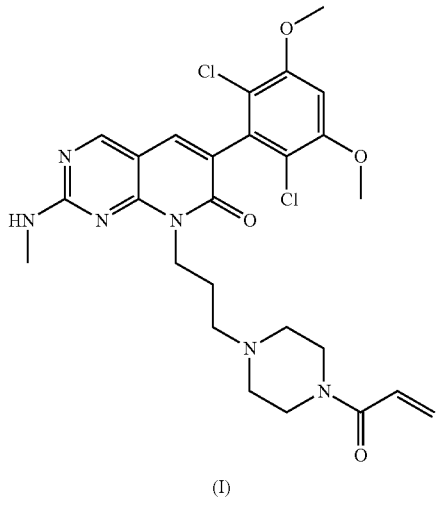
(I)
to provide Compound (I); or
(C) treating a compound of formula (c) with a reducing agent
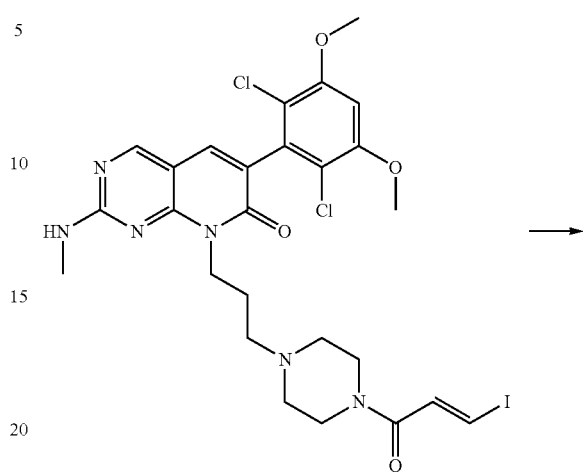
(c)
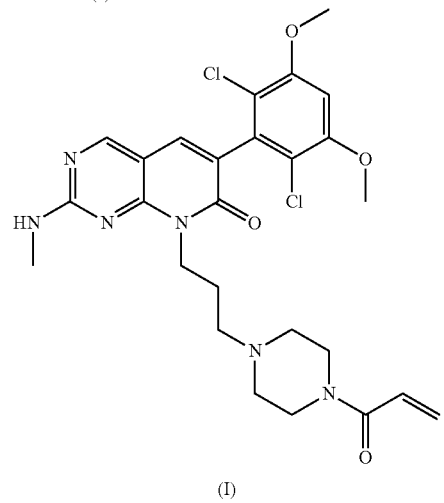
(I)
to provide a compound of Formula (I); or
(D) chlorinating compound (d)
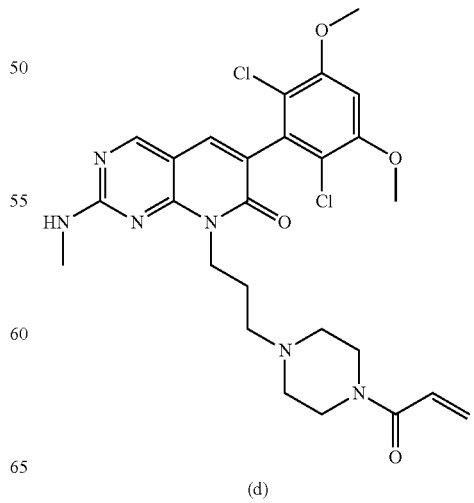
(d)

-continued

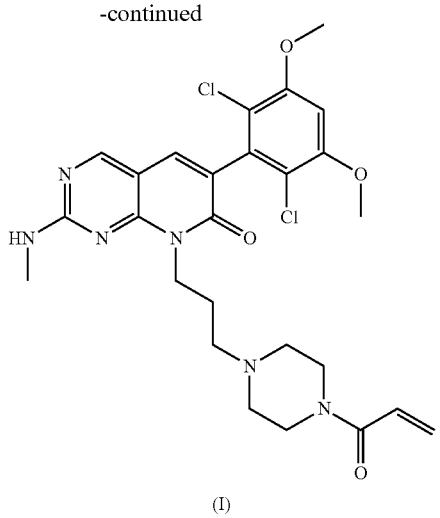

(I)

to provide Compound (I); and (E) optionally converting Compound (I) obtained from reaction (A), (B), (C), or (D) above to an acid addition salt; or (F) optionally converting Compound (I) obtained from reaction (A), (B), (C), or (D) above to the free base.

The process of the first aspect, wherein the process comprises preparing compound (I) via Step (A).

The process of the first aspect, wherein the process comprises preparing compound (I) via Step (B).

The process of the first aspect, wherein the process comprises preparing compound (I) via Step (C).

The process of the first aspect, wherein the process comprises preparing compound (I) via Step (D).

Step A:

In a first embodiment, of the first aspect, the process comprises the process of Step A where X is halo, phosphate, mesylate (methylsulfonate), tosylate (p-methylphenylsulfonate, or 1,1,1-trifluoro-N-[(trifluoromethyl)sulfonate. In a first subembodiment of the first embodiment X is halo such as chloro, bromo, or iodo or phosphate. In a second subembodiment of the first embodiment X is chloro, bromo, or iodo.

In a second embodiment of the first aspect, and the first and second subembodiments contained therein, the process comprises the process of Step A where the reaction is carried out in an aprotic, polar organic solvent, preferably an ether, halogenated organic solvent, or dimethylformamide; more preferable the reaction is carried out in dichloromethane, DMF, acetonitrile, or THF and a like.

In a third embodiment, the first and second embodiments and subembodiments contained therein, the process comprises the process of Step A where the base is either organic or inorganic bases, preferably organic amines, carbonates, bicarbonates, hydrides, hydroxides, e.g., triethylamino, DBU, Na(K)HCO₃, Na(K, Cs)₂CO₃, lithium hydroxide, potassium hydroxide, sodium hydride, sodium methoxide, tert-butoxide, and the like.

In a fourth embodiment of the first aspect, the process comprises the process of Step A is carried under following conditions:

(a) when X is halogen or phosphate; the base is preferably DBU, Et₃N, -tert-butoxide, Na(K)HCO₃, Na(K, Cs)₂CO₃ and the like, and the solvent is preferably dichloromethane, tetrahydrofuran, DMF, and like.

(b) when X is methylsulfonyl; the base is preferably organic amine such as Et₃N, isopropylethylamine, pyridine, and the like, and in organic solvent is preferably CHCl₃, dichloromethane, or THF; or 1,8-diazabicyclo[5.4.0]undec-7-ene (DBU) in tetrahydrofuran (THF);

(c) when X is methanesulfonate or 1,1,1-trifluoro-N-[(trifluoromethyl)sulfonate; the reaction is preferably carried out in the presence of lithium salt (1:1)/THF, NaOMe/MeOH, NaH/dichloromethane, DBU/dichloromethane, potassium amylate, Na(K)butoxide, or NaHCO₃/MeOH;

(d) when X is p-toluenesulfonate, the reaction is carried out preferably in the presence of potassium phthalimide/THF, Et₃N/EtOAc, NaH/THF, NaOMe/MeOH, DABCO/ACN (acetonitrile), or DBU/ACN.

In a fifth embodiment of the first aspect, the process comprises the process of Step B where the reducing agent is Lindlar catalyst.

In a sixth embodiment of the first aspect, the process comprises the process of Step C where the reducing agent is sodium borohydride or i-PrMgCl/THF and a source of proton such as an organic and/or inorganic acid.

Step D:

In a seventh embodiment of the first aspect, the process comprises the process of Step (D) where the chlorinating agent is N-chlorosuccinimide, sulfonyl chloride, sulfuryl chloride. Suitable organic solvents include halogenated hydrocarbon such as dichloromethane when the chlorinating agent is sulfonyl or sulfuryl chloride and organic acid such as acetic acid or halogenated hydrocarbon such as dichloromethane when the chlorinating agent is N-chlorosuccinimide. The reaction may be, preferably the reaction is, carried out in the presence of a base such as diethylamine, pyridine, and the like.

In a second aspect, disclosed is a process of preparing a compound (1):

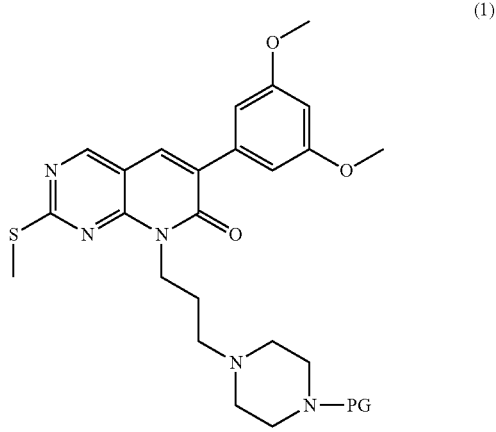

(1)

where PG is a amino protecting group (preferably tert-butoxycarbonyl or benzyloxycarbonyl, more preferably tert-butoxycarbonyl); comprising:

(G) reacting a compound of formula (e):

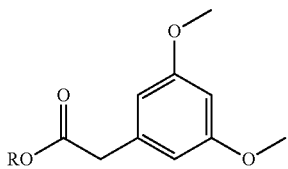

where R is alkyl (preferably methyl or ethyl); with a compound of formula (f):

and
(H) treating a compound of formula (g) formed in situ

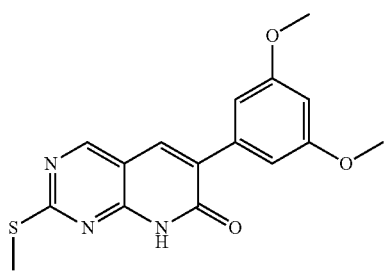

from reaction of compound (e) and (f) with a compound of formula (h) or a salt thereof

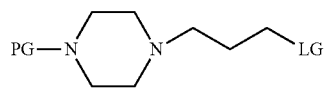

where PG is an amino protecting group (preferably tert-butoxycarbonyl or benzyloxycarbonyl, more preferably tert-butoxycarbonyl) and LG is a leaving group under alkylating reaction conditions (such as halo, tosylate, mesylate, triflate, and the like, preferably mesylate) to provide a compound of formula (1).

In a first embodiment of the second aspect, the process of Step G is where the reaction is carried out in the presence of a base, preferably an inorganic base such as sodium carbonate, potassium carbonate, cesium carbonate, NaH, potassium tert-butoxide, sodium or potassium amylate. In a second embodiment of the second aspect and in the first embodiment contained therein, the reaction is carried out in a polar organic solvent such as dimethylsulfoxide, dimethformamide, dioxane, N—N-methyl-2-pyrrolidone (NMP) or dimethyl-3,4,5,6-tetrahydro-2-pyrimidinone (DMPU), and the like, preferably dimethylsulfoxide. Preferably, the reaction is carried out in the presence of potassium carbonate and cesium carbonate in dimethylsulfoxide at about 50° C.

In a third embodiment of the second aspect and the first embodiment and second embodiments contained therein, the process of Step H is where the reaction is carried out in the presence of a base, preferably inorganic bases such as Na(K)HCO$_3$, Na(K, Cs)$_2$CO$_3$, lithium hydroxide, potassium hydroxide, sodium hydride, sodium methoxide, tert-butoxide, and the like. Preferably the reaction is carried out in a polar organic solvent, preferably in DMSO at about 40° C.

(J) The process of the second aspect, further comprising reacting a compound of formula (1):

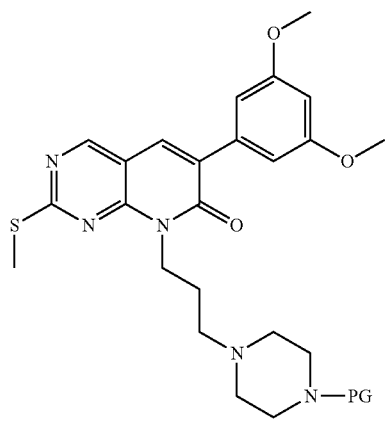

where PG is a amino protecting group (preferably tert-butoxycarbonyl or benzyloxycarbonyl, more preferably tert-butoxycarbonyl; with a chlorinating agent to provide a compound of formula (2) and/or (3):

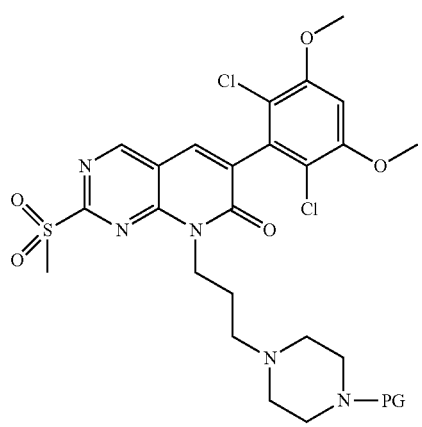

and/or (3)

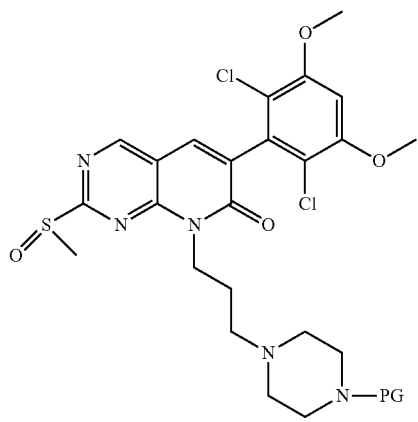

(2)

In a first embodiment of Step (J), the process of Step (J) is performed as described in Step (D) above.

(K) The process of the Step (J), further comprising treating a compound of formula (2) and/or (3):

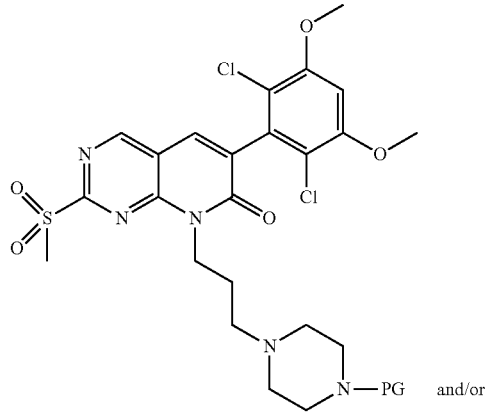

(2) with methylamine to give a compound of (4)

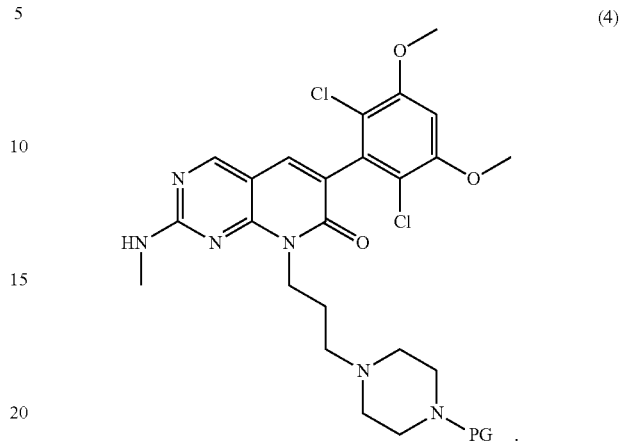

(L) The process of the Step (K), further comprising removing the amino protecting group (PG) in a compound of formula (4):

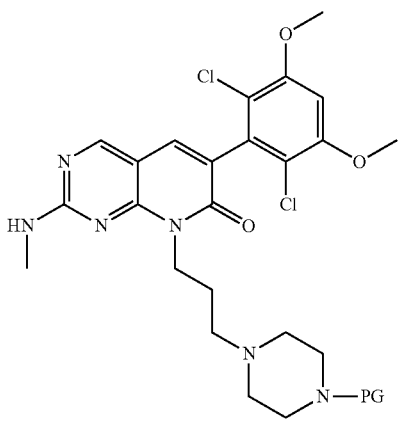

to give a compound of formula (5):

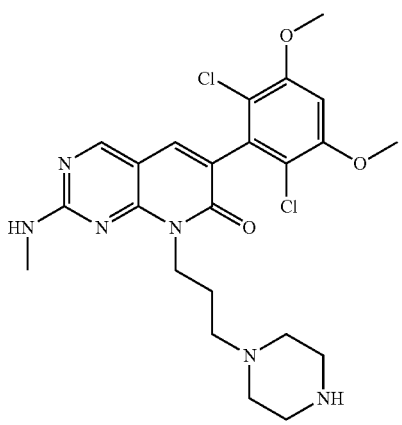 [SMILES: CNc1ncc2cc(-c3c(Cl)c(OC)cc(OC)c3Cl)c(=O)n(CCCN3CCNCC3)c2n1]

(5) or a salt thereof.

In a first embodiment of Step (L), where PG is tert-butoxycarbonyl, it is removed under acidic hydrolysis reaction condition, preferably it is remove with strong acid such as hydrochloric acid, trifluoroacetic acid, and the like, and in a polar organic solvent such as a ketone, an ether, and the like. Where PG is benzyoxycarbonyl or substituted benzyloxycarbonyl, the deprotection of amine is carried out under hydrogenolysis reaction conditions in presence and absence of acids. (M) The process of the Step (L), further comprising reacting a compound of formula (5)

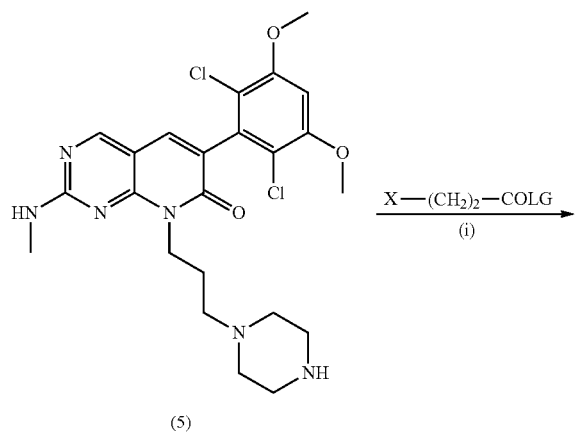

(5)

3-oxide hexafluorophosphate (HATU), hydroxybenzotriazole (HOBt), dicyclohexylcarbodiimide (DCC), and the like, organic base such as $Et_3N$, isopropylethylamine, pyridine, and the like, and in polar organic solvent is preferably $CHCl_3$, dichloromethane, or THF, and the like.

(N) The process of the Step (L), further comprising reacting a compound of Formula (5) with an alkyne of formula (ii) where $LG_1$ is a leaving group under acylation conditions or hydroxy:

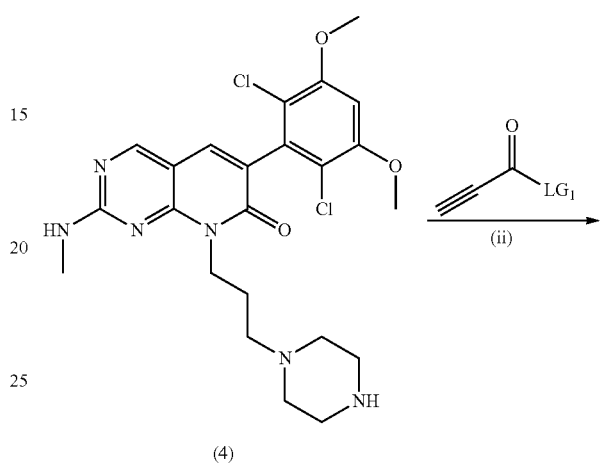

(4)

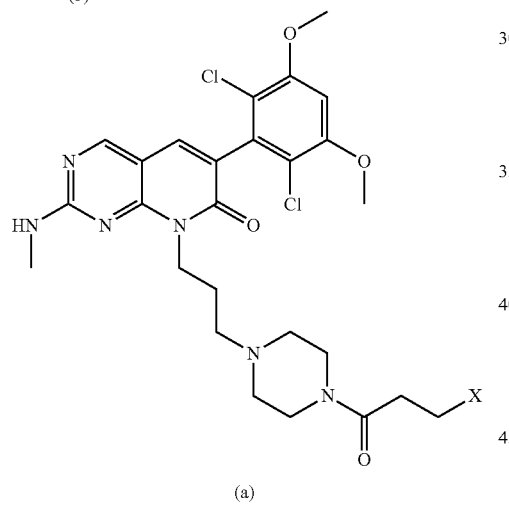

(a)

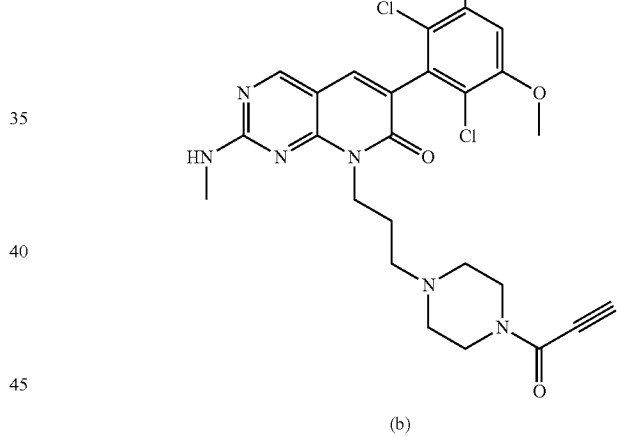

(b)

with a compound of formula (i) where X is a leaving group under elimination reaction conditions and LG is a leaving group under acylation reaction conditions or hydroxyl to give a compound of formula (a).

In a first embodiment of Step (M), the process of Step M the reaction is carried under following conditions:

(a) when LG is halogen; the reaction is carried out in the presence of a base such as $Et_3N$, pyridine, $Na(K)HCO_3$, $Na(K, Cs)_2CO_3$, and the like, and in a polar organic solvents such as dichloromethane, tetrahydrofuran, DMF, acetone, dioxane, N-methylpyridine (NMP), 1,3-Dimethyl-3,4,5,6-tetrahydro-2(1H)-pyrimidinone (DMPU) and the like, and in the presence of a catalyst such as HOBT, DAMP and a like.

(b) when LG=OH; the reaction is carried out under in the presence of activating reagent is preferably 1-ethyl-3-(3-dimethylaminopropyl)carbodiimide (EDCI), 1-[bis(dimethylamino)methylene]-1H-1,2,3-triazolo[4,5-b]pyridinium to give a compound of formula (b).

In a first embodiment of Step N, $LG_1$ is halogen or hydroxyl. In a second embodiment of Step (N): (a) when $LG_1$ is halogen; the reaction is carried out in the presence of a base such as $Et_3N$, $Na(K)HCO_3$, $Na(K, Cs)_2CO_3$ and the like, and in an organic solvent such as dichloromethane, tetrahydrofuran, DMF, and acetone, dioxane, NMP, DMPU and the like, and (b) when $LG_1$ is OH; the reaction is carried out in the presence of an activating reagent such as EDCI, HATU, DCC, and the like, an organic base such as $Et_3N$, isopropylethylamine, pyridine, and the like, in an organic solvent such as $CHCl_3$, dichloromethane, or THF and the like, and a catalyst such as HOBt, DAMP, and the like.

In a third aspect, disclosed in a process of making a compound of formula (d), comprising reacting:

a compound of formula (6) with a compound of formula (iii) where LG is a leaving group under acylating reaction conditions

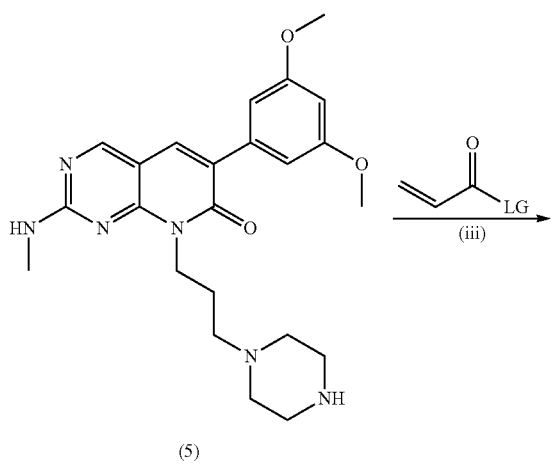

(5)

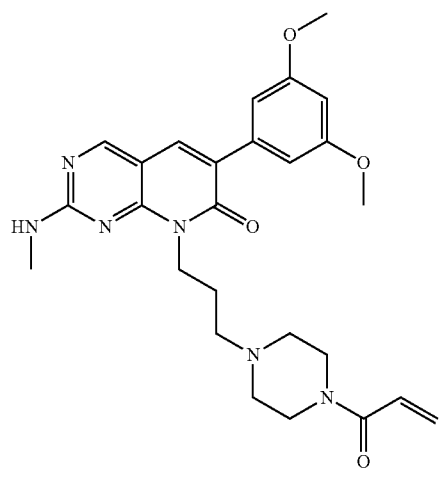

(d)

to give a compound of formula (d).

The reaction conditions are those described for Step N above.

In a fourth aspect, disclosed is an intermediate of formula (6-1):

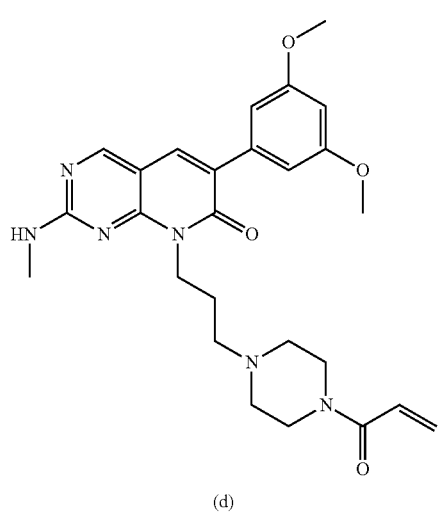

(d)

to give a compound of formula (d); or
reacting a compound of formula (6) with an propenoic acid under amide formation reaction conditions:

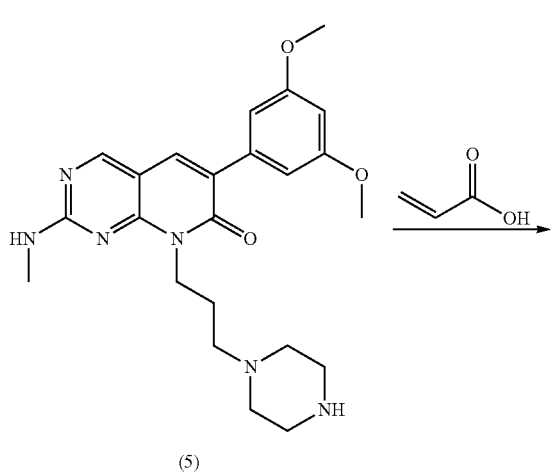

(5)

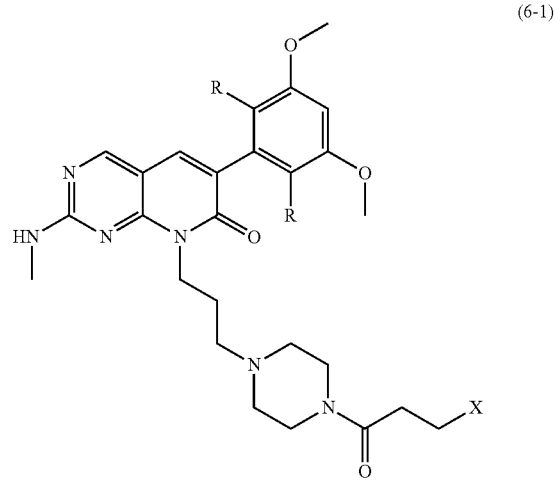

(6-1)

where:
both R are either hydrogen or chloro; and
X is halo, phosphate, tosylate, or mesylate or
a salt thereof.

Aspects of the disclosure are further directed to various solid forms of Compound I, such as different polymorph and/or salt forms. According to one aspect, crystalline 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one is provided.

In one aspect, a crystalline free base of Compound I having the formula below is provided:

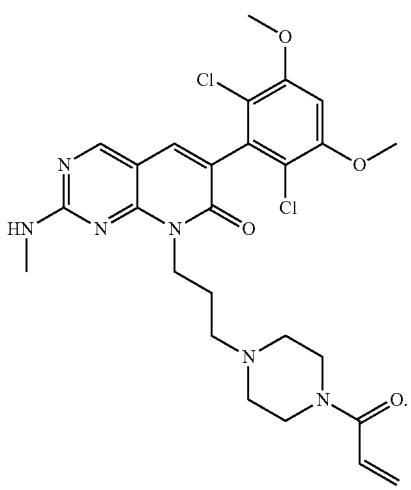 [SMILES: C=CC(=O)N1CCN(CCCn2c(=O)c(-c3c(Cl)c(OC)cc(OC)c3Cl)cc3cnc(NC)nc32)CC1]

In another aspect, the crystalline free base of Compound I is provided that, as characterized by an X-ray powder diffraction (XRPD) pattern, comprises a characteristic peak at about 22° 2Θ (Form 1). In yet another aspect, the Form 1 crystalline free base of Compound I is provided, characterized by an X-ray powder diffraction (XRPD) pattern comprising characteristic peaks at about 15 and 22° 2Θ. In yet another aspect, the Form 1 crystalline free base of Compound I is provided, characterized by an X-ray powder diffraction (XRPD) pattern comprising characteristic peaks at about 12, 15 and 22° 2Θ. In yet another aspect, the Form 1 crystalline free base of Compound I is provided, characterized by an X-ray powder diffraction (XRPD) pattern comprising characteristic peaks at about 7, 11, 12, 15 and 22° 2Θ.

In yet another aspect, the Form 1 crystalline free base of Compound I is provided, characterized by an X-ray powder diffraction (XRPD) pattern comprising characteristic peaks selected from the group consisting of 7, 11, 12, 15, 17, 20 and 22° 2Θ. According to yet another aspect, the Form 1 crystalline free base of Compound I is provided, characterized by an X-ray powder diffraction (XRPD) pattern comprising XRPD 2Θ reflections)(° at one or more of about 7, 11, 12, 15, 17, 20 and 22° 2Θ. According to yet another aspect, the Form 1 crystalline free base of Compound I is provided, characterized by an X-ray powder diffraction (XRPD) pattern comprising XRPD 2Θ reflections (°) at about 7, 11, 12, 15, 17, 20 and 22° 2Θ. In yet another aspect, the Form 1 crystalline free base of Compound I is provided, having an XRPD pattern with one or more peaks corresponding to any of those shown in any of FIGS. 1A-1C. In yet another aspect, the Form 1 crystalline free base of Compound I is provided, having an XRPD pattern substantially as shown in any of FIGS. 1A-1C.

According to yet another aspect, the Form 1 crystalline free base of Compound I is in a substantially anhydrous form.

According to yet another aspect, the Form 1 crystalline free base of Compound I has differential scanning calorimetry (DSC) thermogram with an endotherm having an onset temperature of approximately 201° C., with a melting peak in the range of from approximately 200° C. to 203° C.

Figure 4A:
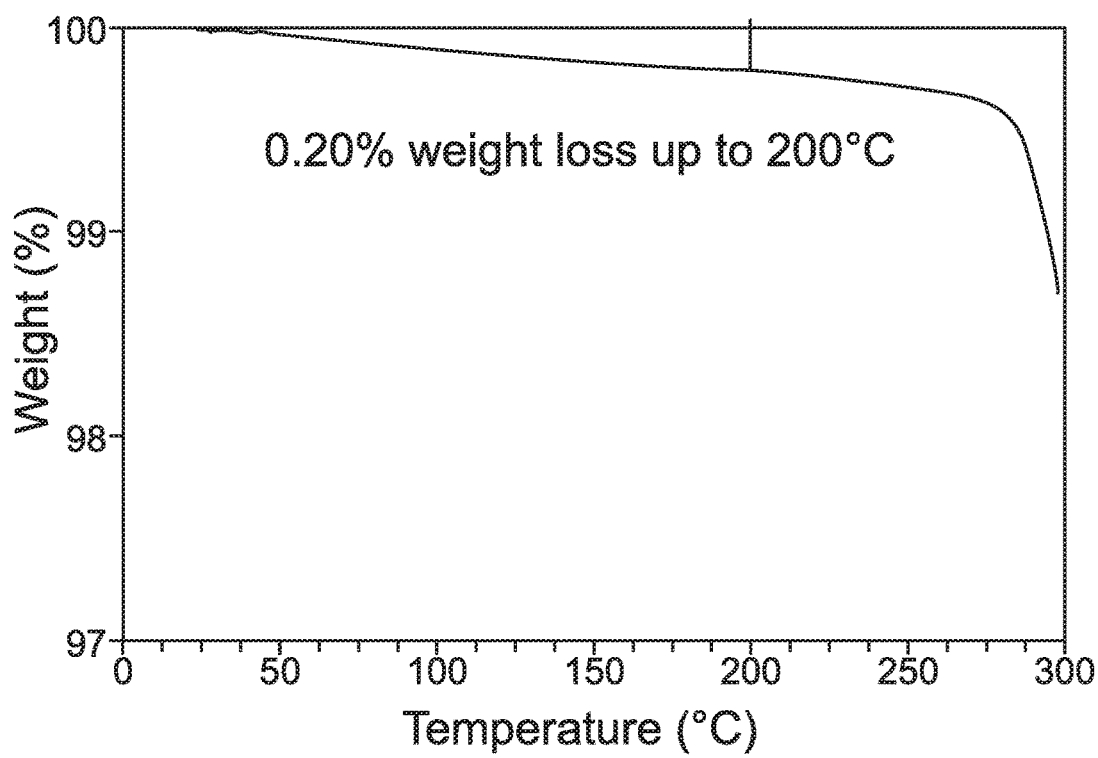
FIG. 4A shows the thermogram obtained by thermogravimetric analysis for Form 1 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.
Figure 4B:
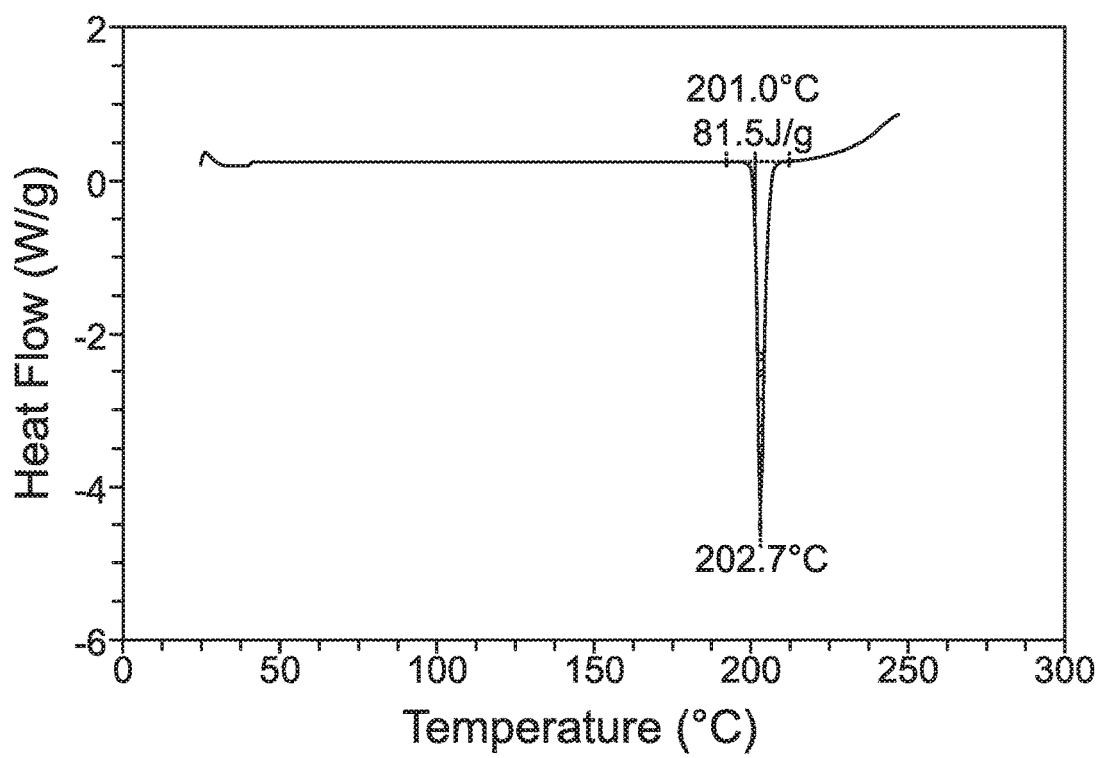
FIG. 4B shows the DSC thermogram for Form 1 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

According to yet another aspect, the Form 1 crystalline free base of Compound I has a DSC thermogram substantially as shown in FIG. 4B.

According to yet another aspect, the Form 1 crystalline free base of Compound I is characterized by having an NMR spectrum with peaks corresponding to any of those in FIG. 3B.

According to yet another aspect, the Form 1 crystalline free base of Compound I is characterized by having a weight loss of 0.20 wt % or less when heated to a temperature of 200° C. as determined by thermogravimetric analysis.

According to yet another aspect, the Form 1 crystalline free base of Compound I is characterized by having a percent weight change of 0.31 wt % or less in an environment having a percent relative humidity of 95% or less.

According to yet another aspect, the Form 1 crystalline free base of Compound I is characterized by being substantially stable in an environment having a percent relative humidity of 93% or less humidity for at least 4 days.

Figure 6:
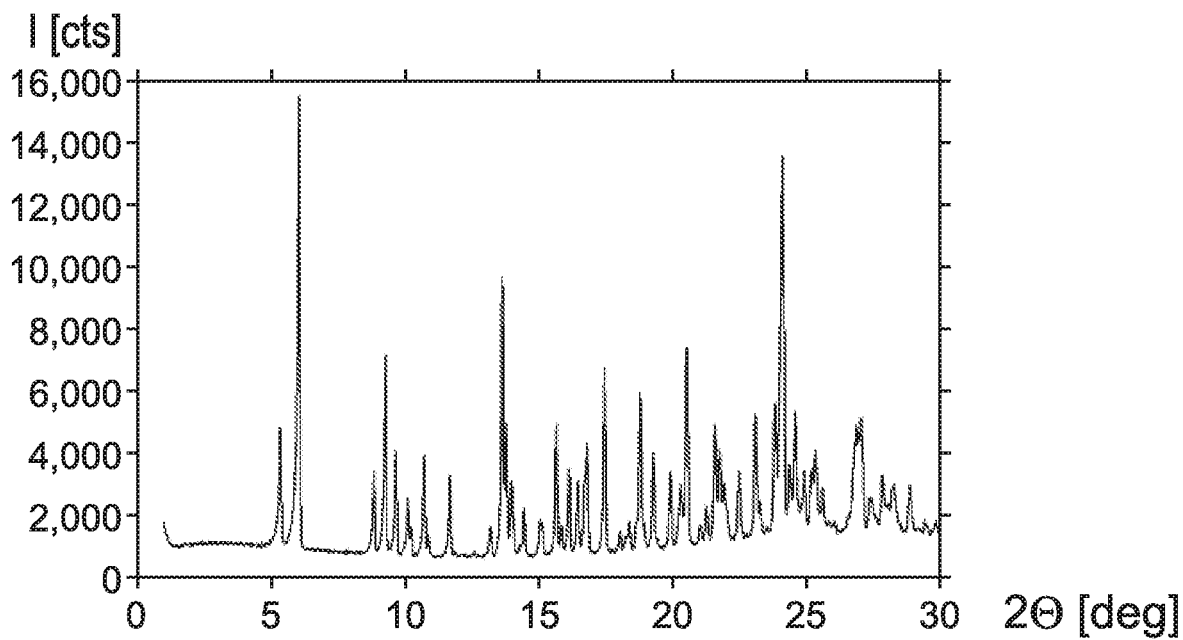
FIG. 6 shows the XRPD spectra of Form 3 (hydrate) of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

According to yet another aspect, a crystalline free base of Compound I is provided that, as characterized by an X-ray powder diffraction (XRPD) pattern, comprises a characteristic peak at about 6° 2Θ (Form 3). According to one aspect, the Form 3 crystalline free base is in a hydrate form. In yet another aspect, the Form 3 crystalline free base of Compound I is provided, characterized by an X-ray diffraction (XRPD) pattern comprising peaks at about 6 and 24° 2Θ. According to yet another aspect, the Form 3 crystalline free base of Compound I is provided characterized by an X-ray powder diffraction (XRPD) pattern comprising characteristic peaks at about 6, 14 and 24° 2Θ. According to yet another aspect, the Form 3 crystalline free base of Compound I is provided characterized by an X-ray powder diffraction (XRPD) pattern comprising characteristic peaks at about 6, 9, 14, 17, 21 and 24° 2Θ. According to yet another aspect, the Form 3 crystalline free base of Compound I is provided, characterized by an X-ray powder diffraction (XRPD) pattern comprising characteristic peaks selected from the group consisting of 5, 6, 9, 14, 17, 21, 24 and 27° 2Θ. According to yet another aspect, the Form 3 crystalline free base of Compound I is provided, characterized by an X-ray powder diffraction (XRPD) pattern comprising XRPD 2Θ reflections (°) at one or more of about 5, 6, 9, 14, 17, 21, 24 and 27. According to yet another aspect, the Form 3 crystalline free base of Compound I is provided, characterized by an X-ray powder diffraction (XRPD) pattern comprising XRPD 2Θ reflections (°) at about 5, 6, 9, 14, 17, 21, 24 and 27. According to yet another aspect, the Form 3 crystalline free base of Compound I is provided, having an XRPD pattern with one or more peaks corresponding to any of those shown in any of FIG. 6. According to yet another aspect, the Form 3 crystalline free base of Compound I is provided, having an XRPD pattern substantially as shown in FIG. 6.

Figure 7:
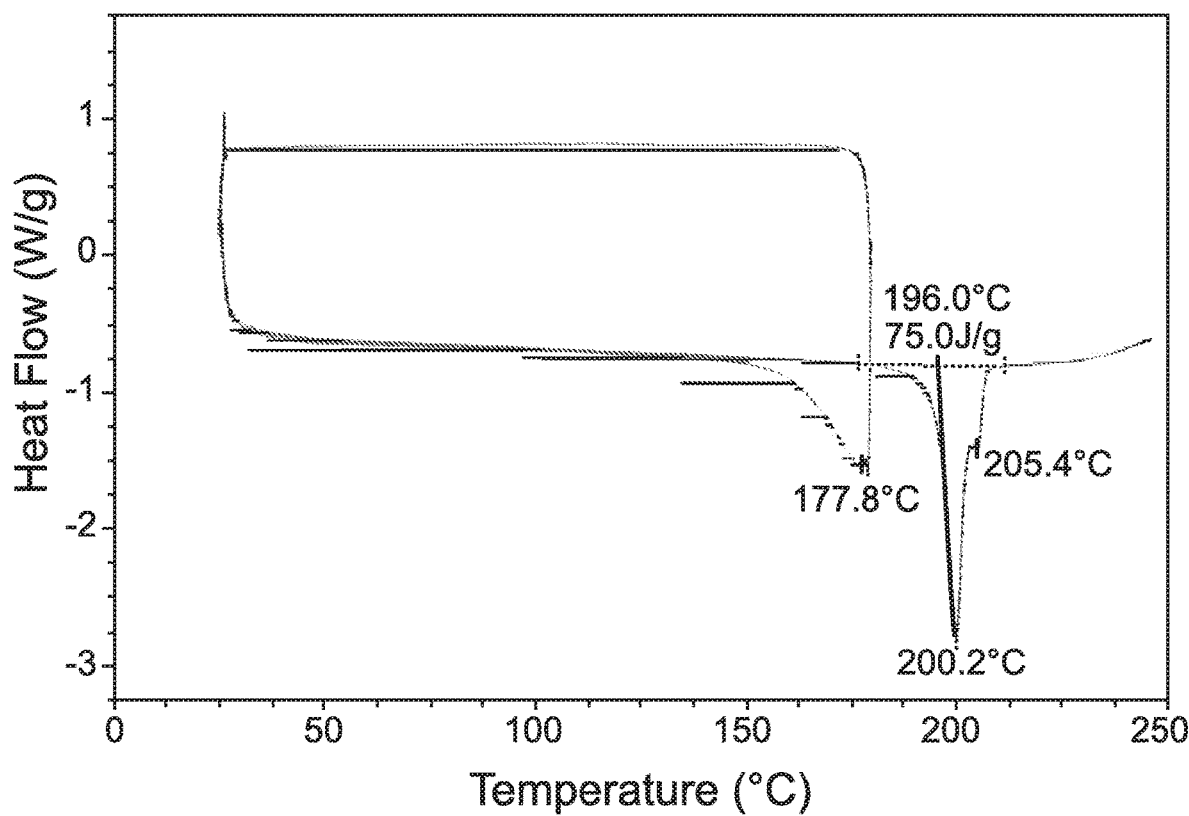
FIG. 7 shows a cycling differential scanning calorimetry (DSC) thermogram obtained for Form 3 (hydrate) of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

According to yet another aspect, the Form 3 crystalline free base of Compound I is characterized by having a differential scanning calorimetry (DSC) thermogram with an endotherm having an onset temperature of approximately 150° C., and having a melting peak at approximately 178° C. In yet another aspect, the Form 3 hydrate of the crystalline free base can dehydrate to Form 1 upon application of cyclic DSC, to provide a material having a differential scanning calorimetry (DSC) thermogram with an endotherm having an onset temperature of approximately 196° C., and having a melting peak in the range of from approximately 200° C. to 203° C. In yet another aspect, the Form 3 crystalline free base of Compound I is characterized by having a cycling differential scanning calorimetry (DSC) thermogram substantially as shown in FIG. 7.

According to yet another aspect, a crystalline free base of Compound I is provided that, as characterized by an X-ray powder diffraction (XRPD) pattern, comprises a characteristic peak at about 14° 2Θ (isostructural solvate family of Forms 7, 10 and 14). According to one aspect, the Forms 7, 10 and/or 14 of the crystalline free base of Compound I are solvate forms. In yet another aspect, the solvate of the crystalline free base of Compound I is at least one of an acetonitrile, acetone and dichloromethane solvate. In yet another aspect, the solvate form of the crystalline free base of Compound I is provided that, as characterized by an X-ray powder diffraction (XRPD) pattern, comprises characteristic peaks at about 8 and 14° 2Θ. In yet another aspect, the solvate form of the crystalline free base of Compound I is provided that, as characterized by an X-ray powder diffraction (XRPD) pattern comprises characteristic peaks at about 8, 14 and 23° 2Θ. In yet another aspect, the solvate form of the crystalline free base of Compound I is provided that, as characterized by an X-ray powder diffraction (XRPD) pattern, comprises characteristic peaks at about 8, 14, 19, 23, 25 and 28° 2Θ. In yet another aspect, the solvate form of the crystalline free base of Compound I is provided that, as characterized by an X-ray powder diffraction (XRPD) pattern, comprises characteristic peaks selected from the group consisting of 8, 12, 14, 19, 21, 23, 25, 26 and 28° 2Θ. According to yet another aspect, the solvate form of the crystalline free base of Compound I is provided that, as characterized by an X-ray powder diffraction (XRPD) pattern, comprises XRPD 2Θ reflections (°) at one or more of about 8, 12, 14, 19, 21, 23, 25, 26 and 28° 2Θ. According to yet another aspect, the solvate form of the crystalline free base of Compound I is provided that, as characterized by an X-ray powder diffraction (XRPD) pattern, comprises XRPD 2Θ reflections (°) at about 8, 12, 14, 19, 21, 23, 25, 26 and 28° 2Θ. According to yet another aspect, the solvate form of the crystalline free base of Compound I is provided, that has an XRPD pattern with one or more peaks corresponding to any of those shown in any of the patterns of FIG. 9. According to yet another aspect, the solvate form of the crystalline free base of Compound I is provided that has an XRPD pattern substantially as shown in any of the patterns of FIG. 9.

Figure 8:
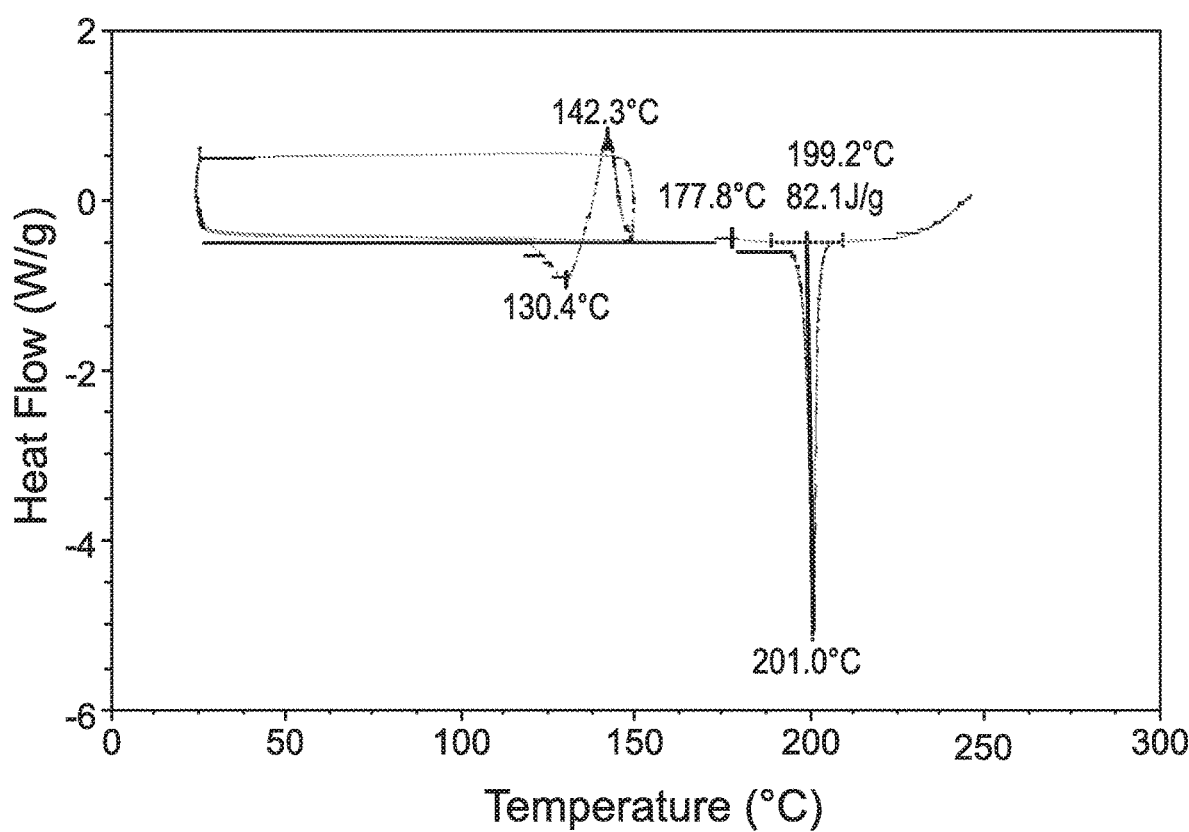
FIG. 8 shows a cycling differential scanning calorimetry (DSC) thermogram obtained for Form 4 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

In yet another aspect, the solvate form (e.g., Forms 7, 10 and/or 14) of the crystalline free base of Compound I is characterized in that desolvation of the crystalline free base solvate results in a material having a differential scanning calorimetry (DSC) thermogram with an endotherm having an onset temperature of approximately 128° C., and having a melting peak at approximately 130° C. According to yet another aspect, the solvate form (e.g., Forms 7, 10 and/or 14) of the crystalline free base of Compound I is characterized in that the desolvation of the crystalline free base and application of cyclic DSC can result in Form 1, with a differential scanning calorimetry (DSC) thermogram having an endotherm with an onset temperature of approximately 199° C., and having a melting peak in the range of from approximately 200° C. to 203° C. According to yet another aspect, the solvate form (e.g., Forms 7, 10 and/or 14) of the crystalline free base of Compound I is characterized in that desolvation of the crystalline free base solvate results in a material having a cycling differential scanning calorimetry (DSC) thermogram substantially as shown in FIG. 8.

According to yet another aspect, a disordered amorphous form of the free base of Compound I is provided. In one aspect, the amorphous form of the free base of Compound I is provided that, as characterized by an X-ray powder diffraction (XRPD) pattern, comprises a characteristic disordered halo at about 23° 2Θ. According to yet another aspect, the disordered amorphous form of the free base of Compound I is provided that, as characterized by an X-ray powder diffraction (XRPD) pattern, comprises characteristic disordered halos at one or more of 23 and 29° 2Θ. In yet another aspect, the disordered amorphous form of the free base of Compound I is provided that, as characterized by an X-ray powder diffraction (XRPD) pattern, comprises characteristic disordered halos at about 23 and 29° 2Θ. According to yet another aspect, the amorphous form of the free base of Compound I is provided, having an XRPD pattern with one or more peaks corresponding to any of those shown in any of patterns of FIG. 10. In yet another aspect, the amorphous form of the free base of Compound I is provided that has an XRPD pattern substantially as shown in any of the patterns of FIG. 10.

According to yet another aspect, a crystalline hydrochloride salt of Compound I is provided. In one aspect, the crystalline hydrochloride salt of Compound I is provided that, as characterized by X-ray powder diffraction pattern (XRPD), comprises a characteristic peak at about 11° 2Θ. In yet another aspect, the crystalline hydrochloride salt of Compound I is provided that, as characterized by X-ray powder diffraction (XRPD) pattern, comprises characteristic peaks at about 11 and 25° 2Θ. According to yet another aspect, the crystalline hydrochloride salt of Compound I is provided that, as characterized by X-ray powder diffraction (XRPD) pattern, comprises characteristic peaks at about 11, 13 and 25° 2Θ. According to yet another aspect, the crystalline hydrochloride salt of Compound I is provided that, as characterized by X-ray powder diffraction (XRPD) pattern, comprises characteristic peaks at about 11, 13, 17 and 25° 2Θ. In yet another aspect, the crystalline hydrochloride salt of Compound I is provided that, as characterized by an X-ray powder diffraction (XRPD) pattern, comprises characteristic peaks selected from the group consisting of about 11, 13, 15 17, 20, 22, 24, 25 and 27° 2Θ. In yet a further aspect, the crystalline hydrochloride salt of Compound I is provided that, as characterized by an X-ray powder diffraction (XRPD) pattern, comprises XRPD 2Θ reflections (°) at one or more of about 11, 13, 15 17, 20, 22, 24, 25 and 27° 2Θ. In yet a further aspect, the crystalline hydrochloride salt of Compound I is provided that, as characterized by an X-ray powder diffraction (XRPD) pattern, comprises XRPD 2Θ reflections (°) at about 11, 13, 15 17, 20, 22, 24, 25 and 27° 2Θ. According to yet another aspect, the crystalline hydrochloride salt of Compound I is provided, having an XRPD pattern with one or more peaks corresponding to any of those shown in FIG. 12. According to yet another aspect, the crystalline hydrochloride salt of Compound I is provided that has an XRPD pattern substantially as shown FIG. 12. In yet another aspect, the crystalline hydrochloride salt of Compound I is provided that is characterized by having an NMR spectrum with peaks corresponding to any of those in FIG. 11.

According to yet another aspect, a crystalline maleate salt of Compound I is provided. In one aspect, the crystalline maleate salt of Compound I is provided that, as characterized by X-ray powder diffraction pattern (XRPD), comprises a characteristic peak at about 22.5° 2Θ. In yet another aspect, the crystalline maleate salt of Compound I is provided that, as characterized by X-ray powder diffraction (XRPD) pattern, comprises characteristic peaks at about 8 and 22.5° 2Θ. According to yet another aspect, the crystalline maleate salt of Compound I is provided that, as characterized by X-ray powder diffraction (XRPD) pattern, comprises characteristic peaks at about 8, 13 and 22.5° 2Θ.

According to yet another aspect, the crystalline maleate salt of Compound I is provided that, as characterized by X-ray powder diffraction (XRPD) pattern, comprises characteristic peaks at about 8, 13, 13.5, 22 and 22.5° 2Θ. In yet another aspect, the crystalline maleate salt of Compound I is provided that, as characterized by an X-ray powder diffraction (XRPD) pattern, comprises characteristic peaks selected from the group consisting of about 8, 10.5, 13, 13.5, 15, 16.5, 22.5 and 23° 2Θ. In yet a further aspect, the crystalline maleate salt of Compound I is provided that, as characterized by an X-ray powder diffraction (XRPD) pattern, comprises XRPD 2Θ reflections (°) at one or more of about 8, 10.5, 13, 13.5, 15, 16.5, 22.5 and 23° 2Θ. In yet a further aspect, the crystalline maleate salt of Compound I is provided that, as characterized by an X-ray powder diffraction (XRPD) pattern, comprises XRPD 2Θ reflections (°) at about 8, 10.5, 13, 13.5, 15, 16.5, 22.5 and 23° 2Θ. According to yet another aspect, the crystalline maleate salt of Compound I is provided, having an XRPD pattern with one or more peaks corresponding to any of those shown in FIG. 14. According to yet another aspect, the crystalline maleate salt of Compound I is provided that has an XRPD pattern substantially as shown FIG. 14. In yet another aspect, the crystalline hydrochloride salt of Compound I is provided that is characterized by having an NMR spectrum with peaks corresponding to any of those in FIG. 13.

Aspects of the disclosure further provide a pharmaceutical composition comprising Compound I in a crystalline and/or salt form, and further comprising a pharmaceutically acceptable carrier and/or excipient.

Aspects of the disclosure may further provide a method of treating diseases mediated by aberrant activity of FGFR, such as cancer, in a subject in need thereof, comprising administering to the subject an effective amount of Compound I in a crystalline and/or salt form.

According to some aspects, the subject is a mammal. According to some aspects, the mammal is selected from the group consisting of humans, primates, farm animals, and domestic animals. According to some aspects, the mammal is a human.

According to some aspects, the method further comprises administering to the subject at least one additional anti-cancer agent.

According to some aspects, a method is provided for treating a cancer in a subject in need thereof comprising administering to the subject an effective amount of a pharmaceutical composition comprising the Compound I in a crystalline and/or salt form.

The term "solid form" is often used to refer to a class or type of solid-state material. One kind of solid form is a "polymorph" which refers to two or more compounds having the same chemical formula but differing in solid-state structure. Salts may be polymorphic. When polymorphs are elements, they are termed allotropes. Carbon possesses the well-known allotropes of graphite, diamond, and buckminsterfullerene. Polymorphs of molecular compounds, such as active pharmaceutical ingredients ("APIs"), are often prepared and studied in order to identify compounds meeting scientific or commercial needs including, but not limited to, improved solubility, dissolution rate, hygroscopicity, and stability.

Other solid forms include solvates and hydrates of compounds including salts. A solvate is a compound wherein a solvent molecule is present in the crystal structure together with another compound, such as an API. When the solvent is water, the solvent is termed a hydrate. Solvates and hydrates may be stoichiometric or non-stoichiometric. A monohydrate is the term used when there is one water molecule, stoichiometrically, with respect to, for example, an API, in the unit cell.

In order to identify the presence of a particular solid form, one of ordinary skill typically uses a suitable analytical technique to collect data on the form for analysis. For example, chemical identity of solid forms can often be determined with solution-state techniques such as $^{13}$C-NMR or $^{1}$H-NMR spectroscopy and such techniques may also be valuable in determining the stoichiometry and presence of "guests" such as water or solvent in a hydrate or solvate, respectively. These spectroscopic techniques may also be used to distinguish, for example, solid forms without water or solvent in the unit cell (often referred to as "anhydrates"), from hydrates or solvates.

Solution-state analytical techniques do not provide information about the solid state as a substance and thus, for example, solid-state techniques may be used to distinguish among solid forms such as anhydrates. Examples of solid-state techniques which may be used to analyze and characterize solid forms, including anhydrates and hydrates, include single crystal X-ray diffraction, X-ray powder diffraction ("XRPD"), solid-state $^{13}$C-NMR, Infrared ("IR") spectroscopy, including Fourier Transform Infrared (FT-IR) spectroscopy, Raman spectroscopy, and thermal techniques such as Differential Scanning calorimetry (DSC), melting point, and hot stage microscopy.

Polymorphs are a subset of crystalline forms that share the same chemical structure but differ in how the molecules are packed in a solid. When attempting to distinguish polymorphs based on analytical data, one looks for data which characterize the form. For example, when there are two polymorphs of a compound (e.g., Form I and Form II), one can use X-ray powder diffraction peaks to characterize the forms when one finds a peak in a Form I pattern at angles where no such peak is present in the Form II pattern. In such a case, that single peak for Form I distinguishes it from Form II and may further act to characterize Form I. When more forms are present, then the same analysis is also done for the other polymorphs. Thus, to characterize Form I against the other polymorphs, one would look for peaks in Form I at angles where such peaks are not present in the X-ray powder diffraction patterns of the other polymorphs. The collection of peaks, or indeed a single peak, which distinguishes Form I from the other known polymorphs is a collection of peaks which may be used to characterize Form I. If, for example, two peaks characterize a polymorph then those two peaks can be used to identify the presence of that polymorph and hence characterize the polymorph. Those of ordinary skill in the art will recognize that there are often multiple ways, including multiple ways using the same analytical technique, to characterize polymorphic polymorphs. For example, one may find that three X-ray powder diffraction peaks characterize a polymorph. Additional peaks could also be used, but are not necessary, to characterize the polymorph up to and including an entire diffraction pattern. Although all the peaks within an entire diffractogram may be used to characterize a crystalline form, one may instead, and typically does as disclosed herein, use a subset of that data to characterize such a crystalline form depending on the circumstances.

For example, as used herein, "characteristic peaks" are a subset of observed peaks and are used to differentiate one crystalline polymorph from another crystalline polymorph. Characteristic peaks are determined by evaluating which observed peaks, if any, are present in one crystalline polymorph of a compound against all other known crystalline polymorphs of that compound to within ±0.2° 2 Θ.

When analyzing data to distinguish an anhydrate from a hydrate, for example, one can rely on the fact that the two solid forms have different chemical structures—one having water in the unit cell and the other not. Thus, this feature alone may be used to distinguish the forms of the compound and it may not be necessary to identify peaks in the anhydrate, for example, which are not present in the hydrate or vice versa.

X-ray powder diffraction patterns are some of the most commonly used solid-state analytical techniques used to characterize solid forms. An X-ray powder diffraction pattern is an x-y graph with the diffraction angle, 2 Θ (°), on the x-axis and intensity on the y-axis. The peaks within this plot may be used to characterize a crystalline solid form. The data is often represented by the position of the peaks on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the art to characterize solid forms.

As with any data measurement, there is variability in X-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts X-rays. Another source of variability comes from instrument parameters. Different X-ray instruments operate using different parameters and these may lead to slightly different diffraction patterns from the same crystalline solid form. Likewise, different software packages process X-ray data differently and this also leads to variability. These and other sources of variability are known to those of ordinary skill in the pharmaceutical arts.

Due to such sources of variability, it is common to recite X-ray diffraction peaks using the word "about" prior to the peak value in degrees (2 Θ) (sometimes expressed herein as "2 Θ-reflections (°)"), which presents the data to within 0.1 or 0.2° (2 Θ) of the stated peak value depending on the circumstances. The X-ray powder diffraction data corresponding to the solid forms of the present invention were collected on instruments which were routinely calibrated and operated by skilled scientists. In the present invention, XRPD values may be obtained using Cu Kα X-ray radiation according to the method described in Example 1. Accordingly, the variability associated with these data would be expected to be closer to ±0.1°2 Θ than to ±0.2°2Θ and indeed likely less than 0.1 with the instruments used herein. However, to take into account that instruments used elsewhere by those of ordinary skill in the art may not be so maintained, for example, all X-ray powder diffraction peaks cited herein have been reported with a variability on the order of ±0.2° 2 Θ and are intended to be reported with such a variability whenever disclosed herein and are reported in the specification to one significant figure after the decimal even though analytical output may suggest higher precision on its face.

Single-crystal X-ray diffraction provides three-dimensional structural information about the positions of atoms and bonds in a crystal. It is not always possible or feasible, however, to obtain such a structure from a crystal, due to, for example, insufficient crystal size or difficulty in preparing crystals of sufficient quality for single-crystal X-ray diffraction.

X-ray powder diffraction data may also be used, in some circumstances, to determine the crystallographic unit cell of the crystalline structure. The method by which this is done is called "indexing." Indexing is the process of determining the size and shape of the crystallographic unit cell consistent with the peak positions in a suitable X-ray powder diffraction pattern. Indexing provides solutions for the three unit cell lengths (a, b, c), three unit cell angles (a, 13, y), and three Miller index labels (h, k, l) for each peak. The lengths are typically reported in Angstrom units and the angles in degree units. The Miller index labels are unitless integers. Successful indexing indicates that the sample is composed of one crystalline phase and is therefore not a mixture of crystalline phases.

IR spectroscopy, particularly FT-IR, is another technique that may be used to characterize solid forms together with or separately from X-ray powder diffraction. In an IR spectrum, absorbed light is plotted on the x-axis of a graph in the units of "wavenumber" ($cm^{-1}$), with intensity on the y-axis. Variation in the position of IR peaks also exists and may be due to sample conditions as well as data collection and processing. The typical variability in IR spectra reported herein is on the order of plus or minus 2.0 $cm^{-1}$. Thus, the use of the word "about" when referencing IR peaks is meant to include this variability and all IR peaks disclosed herein are intended to be reported with such variability.

Thermal methods are another typical technique to characterize solid forms. Different polymorphs of the same compound often melt at different temperatures. Thus, the melting point of a polymorph, as measured by methods such as capillary melting point, DSC, and hot stage microscopy, alone or in combination with techniques such as X-ray powder diffraction, IR spectroscopy, including FT-IR, or both, may be used to characterize polymorphs or other solid forms. Cycling DSC can also be conducted to determine if any particular form converts to a new or existing form. In one aspect, the cycling DSC may show conversion to the most thermally stable form.

As with any analytical technique, melting point determinations are also subject to variability. Common sources of variability, in addition to instrumental variability, are due to colligative properties such as the presence of other solid forms or other impurities within a sample whose melting point is being measured.

Definitions

Unless otherwise stated, the following terms used in the specification and claims are defined for the purposes of this Application and have the following meaning. All undefined technical and scientific terms used in this Application have the meaning as commonly understood by one of ordinary skill in the art to which this invention belongs.

"About" as used herein, unless otherwise specified, means + or −20%, preferably 10% deviation from the listed value. For example, a composition containing about 50 mg by weight of a component may contain 40 mg to 60 mg.

The following examples are provided to further illustrate the compounds, compositions and methods of the present disclosure. These examples are illustrative only and are not intended to limit the scope of the invention in any way.

EXPERIMENTALS

Example 1

Synthesis of Compound (I)

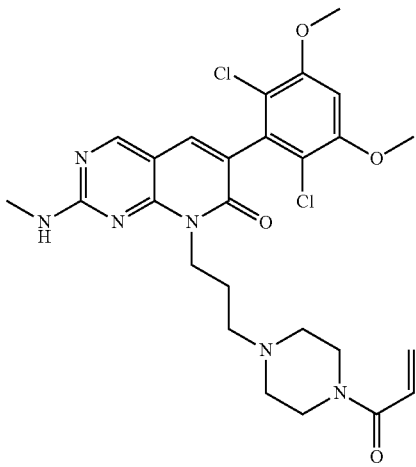 [SMILES: C=CC(=O)N1CCN(CCCn2c(=O)c(-c3c(Cl)c(OC)cc(OC)c3Cl)cc3cnc(NC)nc32)CC1]

Step 1

2-(3,5-Dimethoxyphenyl)acetic acid (1000 g) was charged into appropriately sized three-neck RBF equipped with a condenser and dissolved with methanol (10 L). Concentrated sulfuric acid (20 g) was added and a solution was brought to gentle boiling. Reaction progress was monitored by HPLC. The reaction mixture was transferred to appropriately sized RBF and concentrated to ca. 3 L. and then co-evaporated with DMSO (3 L) to about 4 L and the residue containing methyl 2-(3,5-dimethoxyphenyl)acetate (1071 g) was telescoped to Step 2.

Step 2

To an appropriate reactor equipped with mechanical stirrer methyl 2-(3,5-dimethoxyphenyl)acetate (1071 g) in DMSO (3.2 L), 4-amino-2-(methylthio)-pyrimidine-5-carbaldehyde (819 g, 0.95 eq.), potassium carbonate (1057 g, 1.5 eq.) and cesium carbonate (249 g, 0.15 eq.) was charged and the mixture was stirred at 50° C. After 15 h, the mixture containing 6-(3,5-dimethoxyphenyl)-2-(methylthio)pyrido[2,3-d]pyrimidin-7(8H)-one was cooled to RT. Potassium carbonate (854 g, 1.2 eq.) and tert-butyl 4-(3-((methylsulfonyl)oxy)propyl)piperazine-1-carboxylate HCl (2112 g, 1.1 eq.) was charged. Upon completion of the reaction, ethyl acetate and water were added.

Organic layer was separated and aqueous layer was extracted with ethyl acetate. Combined organic layers were washed with 25% aqueous solution of sodium chloride. Organic phase was dried over anhydrous magnesium sulfate. Drying agent was filtered off and washed with ethyl acetate. The filtrate was concentrated to ca. 9.6 L. and cooled to 0-5° C. A solution of p-toluenesulfonic acid (970 g, 1.0 eq.) in ethyl acetate (4.28 L) was added dropwise. The resulted suspension was slowly warmed to RT and stirred for 5 h. Solids were filtered off, washed with ethyl acetate and dried give tert-butyl-4-(3-(6-(3,5-dimethoxyphenyl)-2-(methylthio)-7-oxopyrido[2,3-d]pyrimidin-8(7H)-yl)propyl)piperazine-1-carboxylate 4-methylbenzenesulfonate.

Step 3

To an appropriate reactor equipped with mechanical stirrer was charged acetic acid (12 L), 6-(3,5-dimethoxyphenyl)-2-(methylthio)pyrido[2,3-d]pyrimidin-7(8H)-one (2000 g) and triethylamine (639 g, 2.3 eq.). Internal temperature was adjusted to approximately 20° C. and N-chlorosuccinimide (1651 g, 4.5 eq.) was added at 20-30° C. Reaction was stirred for 2 hours. Ethyl acetate (30 L) was added. 5% aqueous NaCl solution (20 L) was added. The organic layer was separated and the aqueous layer was extracted with EtOAc. The combined organic layers were washed with 30% aqueous potassium carbonate solution (14 L). The organic layer was concentrated to ~12 L and used for next step directly.

Step 4

To tert-butyl-4-(3-(6-(2,6-dichloro-3,5-dimethoxyphenyl)-2-(methylsulfonyl)-7-oxopyrido[2,3-d]pyrimidin-8(7H)-yl)propyl)piperazine-1-carboxylate (1804 g) in ethyl acetate extract (12 L) from Step 3, was added 2M methylamine solution in THF (3435 mL) was slowly added maintaining temperature below 30° C. After reaction was complete, the suspension concentrated to 3.3 L and ethyl acetate (6 L) was added. The mixture was heated at 50° C. for 2 h, and then cooled to RT. Solids were filtered off and washed with ethyl acetate, water and dried to give tert-butyl-4-(3-(6-(2,6-dichloro-3,5-dimethoxyphenyl)-2-(methylamino)-7-oxopyrido[2,3-d]pyrimidin-8(7H)-yl)propyl)piperazine-1-carboxylate (1845 g).

Step 5 tert-Butyl-4-(3-(6-(2,6-dichloro-3,5-dimethoxyphenyl)-2-(methylamino)-7-oxo-pyrido[2,3-d]pyrimidin-8(7H)-yl)propyl)piperazine-1-carboxylate (125 g) was charged into appropriately sized three-neck RBF equipped with a condenser and suspended in acetone (1000 mL). Concentrated (36%) aqueous hydrochloric acid (100 mL) was slowly added and the mixture was heated to 45° C. for 1 h. the reaction mixture was gradually cooled to RT over 4 h and filtered, washed with acetone and dried to give tert-butyl-4-(3-(6-(2,6-dichloro-3,5-dimethoxyphenyl)-2-(methylamino)-7-oxopyrido[2,3-d]pyrimidin-8(7H)-yl)propyl)piperazine-1-carboxylate•3HCl (125 g) in 98% yield.

Step 6

To an appropriate reactor tert-butyl-4-(3-(6-(2,6-dichloro-3,5-dimethoxyphenyl)-2-(methylamino)-7-oxopyrido[2,3-d]pyrimidin-8(7H)-yl)propyl)piperazine-1-carboxylate (50 g) and DMF (500 mL) was charged while stirring at RT. The suspension was cooled to 0-5° C. and saturated aqueous sodium bicarbonate solution (375 mL) was slowly added maintaining temperature below 15° C. with emission of $CO_2$. The mixture was cooled again to 0-5° C. and acryloyl chloride (8.6 mL, 1.3 eq.) was slowly added at temperature below 10° C. Once acryloyl chloride addition was finished the reaction mixture was gradually warmed to RT over 1 h. Saturated aqueous sodium bicarbonate solution (75 mL) was slowly added and the resulted mixture was heated at 45-55°

C. for 0.5-1.5 h. It was then gradually cooled to RT and stirred for another 0.5-1.5 h. Solids were filtered off, washed with water and dried.

Crude product was dissolved in dichloromethane (750 mL) at reflux and the solution was cooled to ambient temperature. Silica gel (7.5 g) was added while stirring. After 30 min. the mixture was filtered through Celite and the filtering bed was washed with dichloromethane. Ethyl acetate (250 mL) was added and the solution was concentrated under reduced to about 250 mL at 40-50° C. Ethyl acetate (450 mL) was slowly added at 50° C. After 30 min. the suspension was slowly cooled to 40° C. and solids were filtered off, washed with ethyl acetate and dried to give 36 g of 8-(3-(4-acryloylpiperazin-1-yl)propyl)-6-(2,6-dichloro-3,5-dimethoxyphenyl)-2-(methylamino)pyrido[2,3-d]pyrimidin-7(8H)-one in 82%. XRPD analysis of the product showed an XRPD pattern for a highly crystalline compound, which was assigned as Form 1 (discussed in further detail below).

Example 2—Free Base Forms

Method of Analysis
X-Ray Powder Diffraction

XRPD patterns were obtained with a PANalytical X'Pert PRO MPD diffractometer using an incident beam of Cu radiation (1.54059 angstroms) produced using an Optix long, fine-focus source. The diffractometer was configured using the symmetric Bragg-Brentano geometry. Prior to analysis, a silicon sample (NIST SRM 640e) was analyzed to verify the observed position of the Si 111 peak was consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening fro axial divergence. Diffraction patterns were collected using a scanning position-sensitive detector located 240 mm from the sample.

Proton NMR Spectroscopy

Proton NMR Spectroscopy was performed by acquiring solution NMR spectra with an Agilent DD2-400 spectrometer. Samples were prepared by dissolving a given amount of sample in DMSO-$d_6$ containing tetramethylsilane (TMS).

Differential Scanning Calorimetry

Differential Scanning calorimetry (DSC) was performed with a TA Instruments 2920 or Q200 differential scanning calorimeter. Temperature calibration was performed using a NIST-traceable indium metal. The sample was placed into an aluminum Tzero crimped pan and the weight was accurately recorded. A weighed aluminum pan configured as the sample pan was placed on the reference side of the cell.

Thermal Gravimetric Analysis

Thermal Gravimetric Analysis (TGA) was performed using a TA Instruments Discovery thermographic analyzer, with temperature calibration being performed using nickel and Alumel™. Each sample was placed in a pan, hermetically sealed, the lid pierced, and then inserted into the thermal gravimetric furnace which was heated under nitrogen.

Dynamic Vapor Sorption/Desorption (DVS)

Dynamic Vapor Sorption/Desorption (DVS) data was collected on a VTI SGA-100 Vapor Sorption Analyzer, using NaCl and PVP as calibration standards. Samples were not dried prior to analysis. Sorption and desorption data were collected over a range from 5% to 95% relative humidity (RH) at 10% RH increments under a nitrogen purge. The equilibrium criterion used for analysis was less than 0.01000% weight change in 5 minutes with a maximum equilibration time of 3 hours. Data were not corrected for the initial moisture content of the samples.

Polymorphs of Compound (I) Free Base

Form 1

Figure 1B:
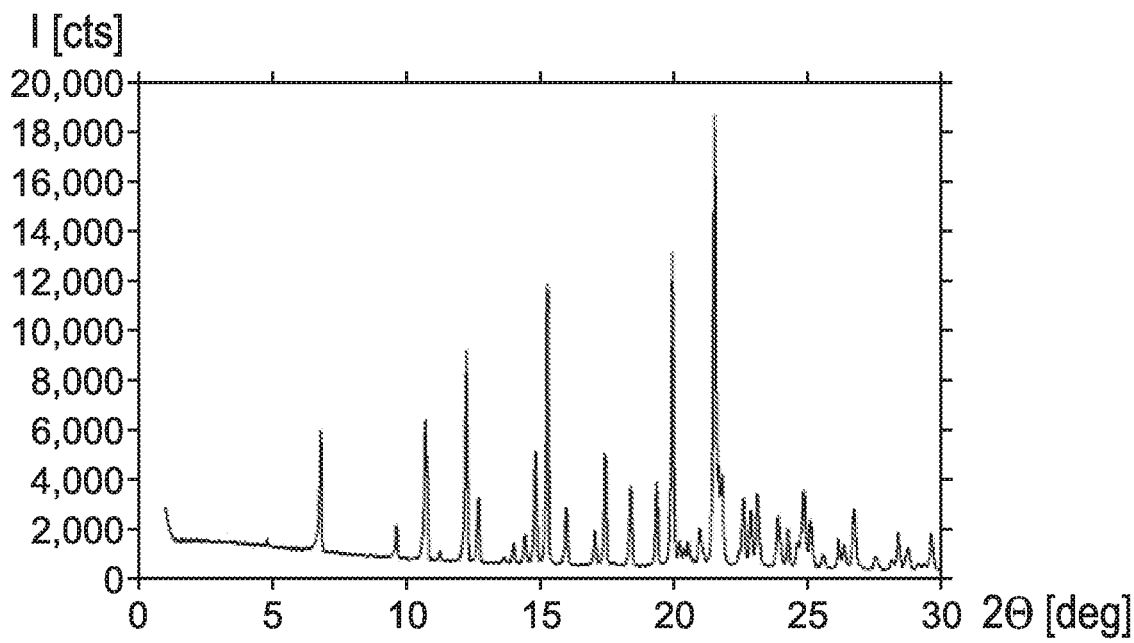
Figure 1C:
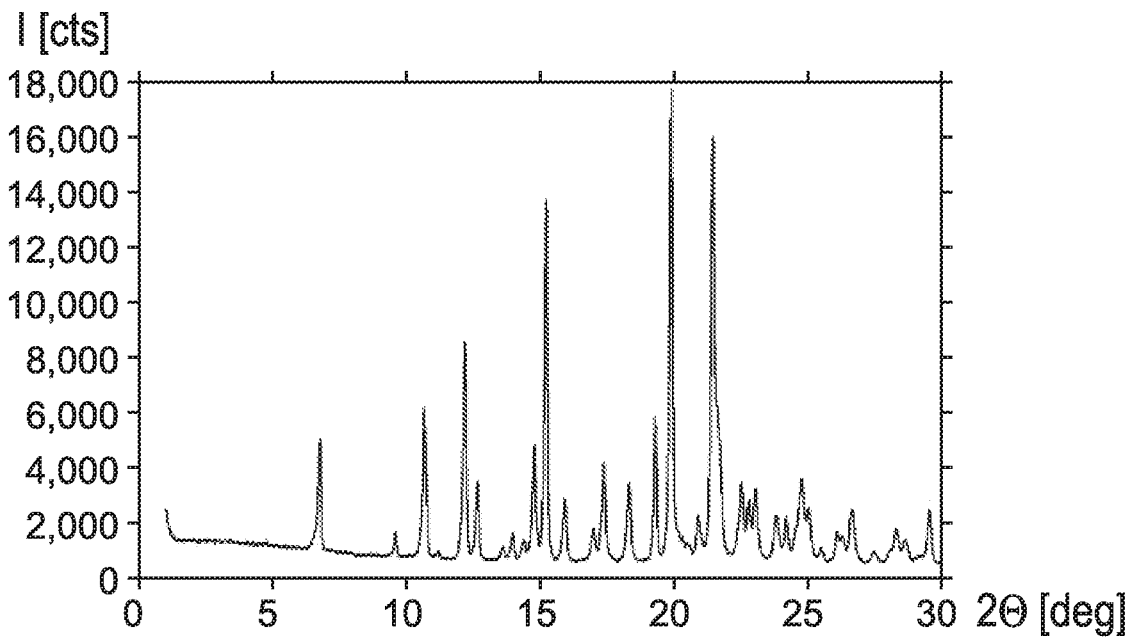

The crystalline polymorph corresponding to Form 1 of the Compound (I) free base was prepared from three samples (Samples 1-3). Sample 1 containing Form 1 was obtained by the synthetic method described in Example 1 above, and the XRPD spectrum for this Sample 1 is shown in FIG. 1A. Sample 2 containing Form 1 was obtained from a heptane slurry of Sample 1, and the XRPD spectrum for this Sample 2 is shown in FIG. 1B. Sample 3 containing Form 1 was obtained from a THF slow cool process of Sample 1, and the XRPD spectrum for this Sample 3 is shown in FIG. 1C.

Figure 2:
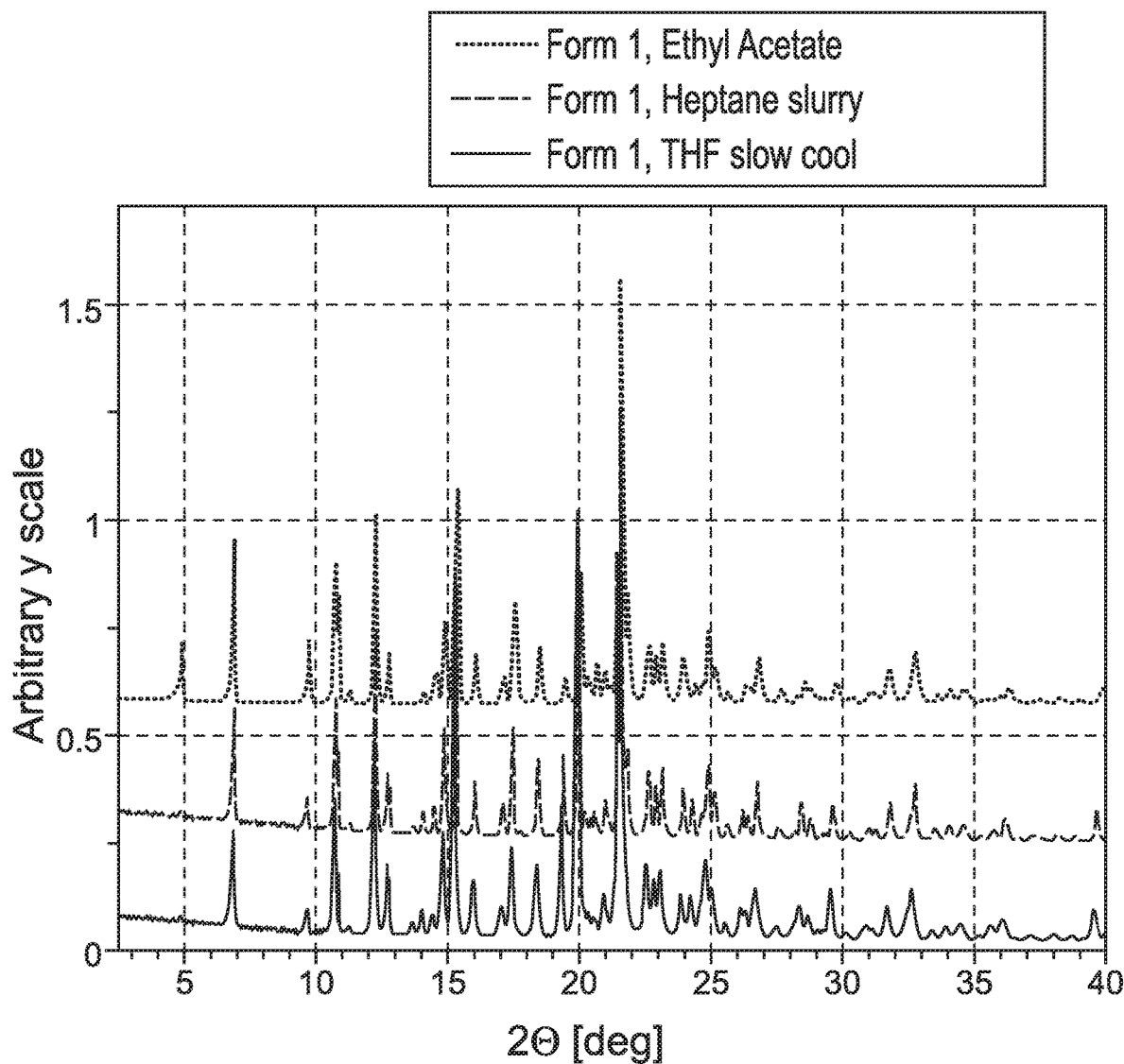
FIG. 2 shows a comparison of the XRPD spectra of Samples 1-3 of Form 1 of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

FIG. 2 shows a comparison of the three XRPD spectra (FIGS. 1A-1C) obtained for Samples 1-3 of Form 1, and shows that the XRPD spectra exhibit the same crystalline form, albeit with slight variations in peak locations. In particular, the crystalline forms can be understood to have a flexible crystal framework that may slightly expand or contract with changes in, for example, temperature and pressure, such that the 2Θ values of the characteristic peaks in an XRPD spectrum for Form 1 may vary by slightly between individual spectra. Peaks shown in FIGS. 1A-1C are listed in Table 1, with prominent peaks listed in Table 2.

TABLE 1

| Form 1 XRPD Peaks | |
|---|---|
| 2Θ value | Intensity (cts) |
| 7 | 16,000 |
| 11 | 15,000 |
| 12 | 19,000 |
| 15 | 21,000 |
| 17 | 10,000 |
| 20 | 12,000 |
| 22 | 45,000 |

TABLE 2

| Prominent XRPD Peaks - Form 1 | |
|---|---|
| 2Θ value | Intensity (cts) |
| 7 | 16,000 |
| 11 | 15,000 |
| 12 | 19,000 |
| 15 | 21,000 |
| 22 | 45,000 |

FIGS. 1A-1C further list the indexing information for Form 1 as obtained from each of the XRPD spectra, including the size and shape of the crystallographic unit cell as determined according to the peak positions in the diffraction pattern. Indexing of Form 1 from the XRPD spectra in FIGS. 1A-1C yielded the potential for an additional free volume of approximately 45 Å$^3$ per formula unit for the Sample 1, as shown in FIG. 1A, which could theoretically accommodate 2 moles of water per mole of the compound. Sample 3 yielded a free crystal volume of approximately 59 Å$^3$, whereas Sample 2 had a free crystal volume somewhere in between Sample 1 (i.e., in a contracted state) and Sample 3 (i.e., in an expanded state). Thus, Form 1 is believed to have a crystal framework that exists in a slightly expanded and contracted state, where the crystal form exhibits minor unit cell changes as a function of temperature, pressure, and composition, but nonetheless corresponds to the same crystal form.

Figure 3A:
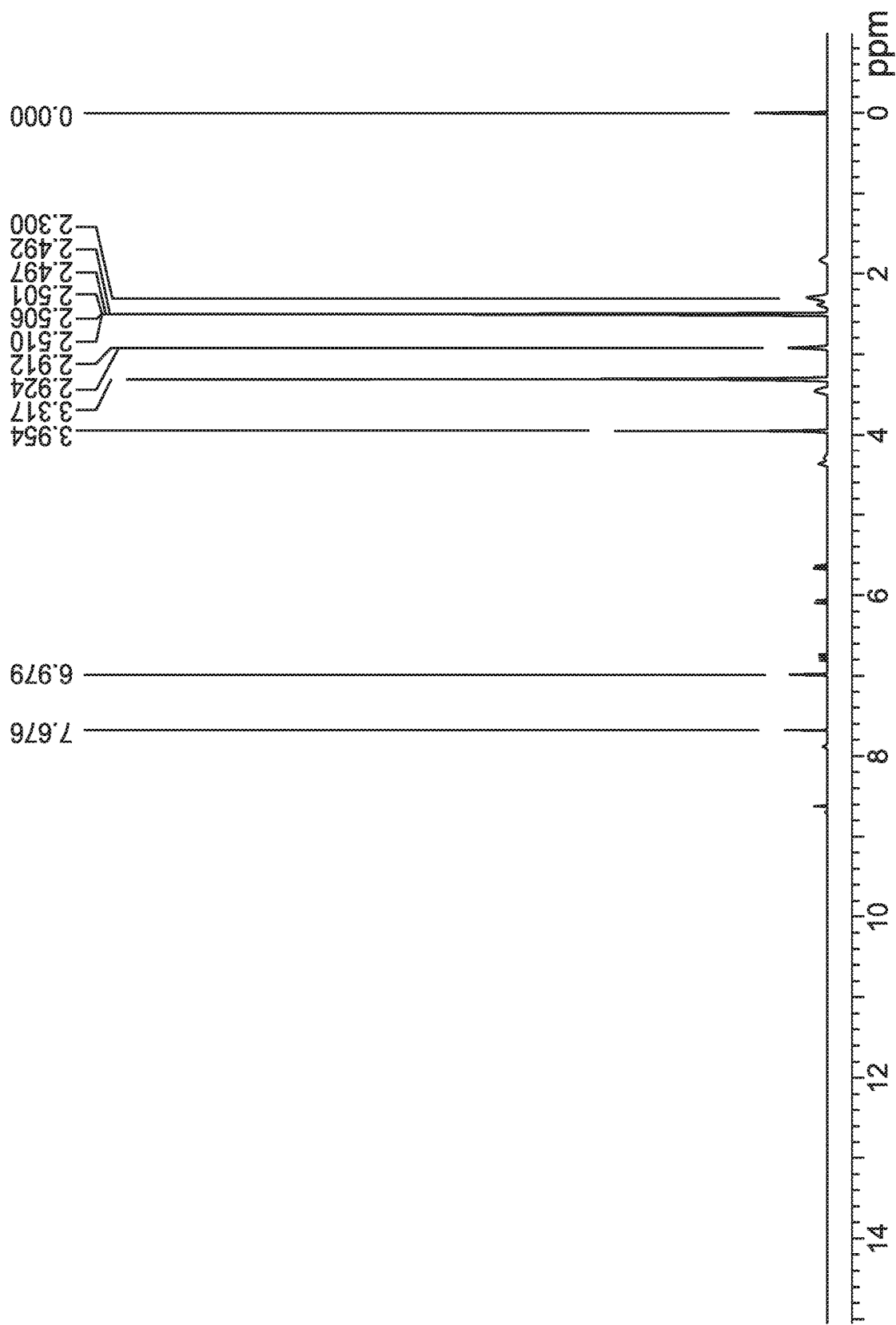
FIG. 3A shows the proton NMR spectrum of Form 1 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

The $^1$H NMR spectrum for Form 1 is shown in FIG. 3A, and the chemical shifts are listed in FIG. 3B. This $^1$H NMR spectrum is consistent with the chemical structure of Compound (I), with the chemical shifts at 2.5 ppm and 3.3 ppm assigned to residual NMR solvent protons, DMSO and water, respectively.

The differential scanning calorimetry (DSC) curve for Form 1 is shown in FIG. 4B. The differential scanning curve exhibited a single endotherm starting at about 201° C. (i.e., temperature of endotherm onset), and a melting peak at approximately 202.7° C. (i.e., in a range of from approximately 200° C. to 203° C.). The thermogram obtained for the thermogravimetric analysis (TGA) of Form 1 is shown in FIG. 4A. Negligible weight loss up to 200° C. of about 0.20% or less was observed.

Figure 5:
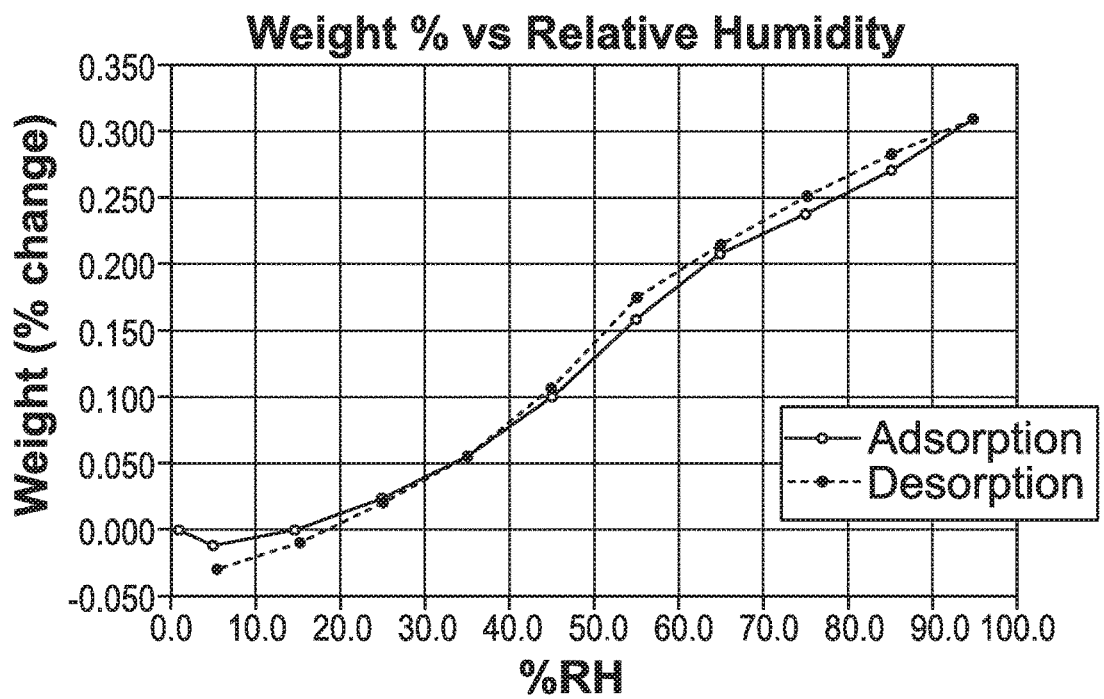
FIG. 5 shows the dynamic vapor sorption (DVS) isotherm for Form 1 of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

FIG. 5 illustrates a dynamic vapor sorption (DVS) isotherm of Form 1, indicating negligible weight gain in each sorption cycle and no hysteresis upon desorption, thus demonstrating that Form 1 is not hygroscopic. In particular, the isotherm for Form 1 exhibited a weight percent change of about 0.31 wt % or less (0.309 wt %) up to a percent relative humidity of about 95% (94.79%). Furthermore, evaluation of the sample after DVS testing via XRPD analysis showed the sample maintained crystal peaks corresponding to those identified as being characteristic of Form 1, indicating that a phase change did not occur with the exposure to humidity in the DVS testing. Also, the XRPD spectrum of a sample of Form 1 exposed to 93% relative humidity for four days at ambient temperature did not result in any changes in form observable by XRPD. This data indicated that Form 1 was physically stable at elevated humidity. Furthermore, the thermal and DVS data showed that Form 1 is a substantially anhydrous form, even though the crystal structure of Form 1 is theoretically capable of accommodating a plurality of molar equivalents of water, as determined by indexing of the XRPD data.

Furthermore, while solvated and/or hydrated forms of Compound (I) can be prepared, as discussed in further detail below, these forms may tend to show conversion to Form 1, such as upon heating of the Forms to a temperature of 180° C. or more.

Hydrate Form

A crystalline polymorph hydrate form corresponding to Compound (I) was prepared by using a 50:50 acetone/water slurry, and is referred to herein as Form 3. The XRPD spectrum for Form 3 is shown in FIG. 6. Form 3 was shown to dehydrate to Form 1 when exposed to elevated temperatures above 180° C. The XRPD data was of sufficient quality to be indexed, indicating that the material is primarily a single crystalline phase, as shown in FIG. 6. Form 3 has a larger estimate volume per formula unit than would be expected for an anhydrous form, and the additional free volume can theoretically accommodate approximately 0.8 to 1.3 moles of water per mole of Compound (I). Also, similarly to Form 1, the XRPD peak positions may appear slightly shifter with minor unit-cell changes. Peaks shown in FIG. 6 are listed in Table 3, with prominent peaks listed in Table 4.

TABLE 3

Form 3 XRPD Peaks - Hydrate

| 2Θ value | Intensity (cts) |
|---|---|
| 5 | 4,500 |
| 6 | 15,500 |
| 9 | 7,000 |
| 14 | 10,000 |
| 17 | 6,000 |
| 21 | 8,000 |
| 24 | 14,000 |
| 27 | 5,000 |

TABLE 4

Form 3 Prominent XRPD Peaks - Hydrate

| 2Θ value | Intensity (cts) |
|---|---|
| 6 | 15,500 |
| 9 | 7,000 |
| 14 | 10,000 |
| 17 | 6,000 |
| 21 | 8,000 |
| 24 | 14,000 |

FIG. 6 further list the indexing information for Form 3 as obtained the XRPD spectra, including the size and shape of the crystallographic unit cell as determined according to the peak positions in the diffraction pattern.

FIG. 7 shows the results of a cycling DSC experiment, in which Form 3 was heated to 180° C., past the desolvation endotherm, and held isothermally for one minute before cooling back down and repeating the DSC analysis. An initial melt endotherm for the Form 3 crystalline free base of Compound I has an onset at temperature of approximately 150° C., with a melting peak at approximately 178° C. Cycling DSC further shows a melt endotherm having an onset at about 196° C., with a melting peak at approximately 200.2° C. (i.e., in the range of approximately 200° C. to 203° C.), and the cycling DSC appears to show that the phase change from desolvation was not reversible. Additional physical stability information suggest that the final melt endotherm, although consisting of multiple overlapping events, is that of Form 1, consistent with Form 3 dehydrating to Form 1 when exposed to elevated temperatures.

Solvate Forms

Crystalline polymorph solvate forms of Compound (I) were prepared, by using solvent/antisolvent from DCM/ACN (Form 7), cooling from acetone (Form 10), and using a slurry in DCM (Form 14). A further polymorph form (Form 4) was generated through the desolvation of Form 7 from acetonitrile (e.g., exposure to 65° C. under vacuum for 1 day). The Forms 7, 10 and 14 correspond to a family of isostructural solvates, and Form 4 is believed to be unsolvated/anhydrous. Solvates were also generated from THF, methanol, ethanol and 1,4-dioxane.

Referring to FIG. 8, a cycling DSC experiment is shown that illustrates the relationship between Form 4 (generated from desolvation of an isostructural solvate) and Form 1 discussed above. In the experiment, the material was heated to 150° C., and held isothermally for one minute before cooling back down and repeating the DSC analysis. The Form 4 that is the desolvated form of the isostructural solvates (Forms 7, 10 and 14) has a differential scanning calorimetry (DSC) thermogram with an endotherm having an onset temperature of approximately 128° C., and having a melting peak at approximately 130° C. A subsequent melt endotherm is exhibited in cycling DSC with an onset at approximately 199° C., and having a melting peak at approximately 201.0° C. (i.e., in a range of from approximately 200° C. to 203° C.). Additional physical stability information suggests that an initial endo/exotherm event is conversion to another material, and that the small exotherm and final melt endotherm is conversion to and melt of Form 1 described above. This data is consistent with complete conversion to Form 1 from any of the family of isostructural solvates (Forms 7, 10 and 14), or a material generated by desolvation of these isostructural solvates (e.g. Form 4), with exposure to elevated temperatures above 180° C.

Figure 9:
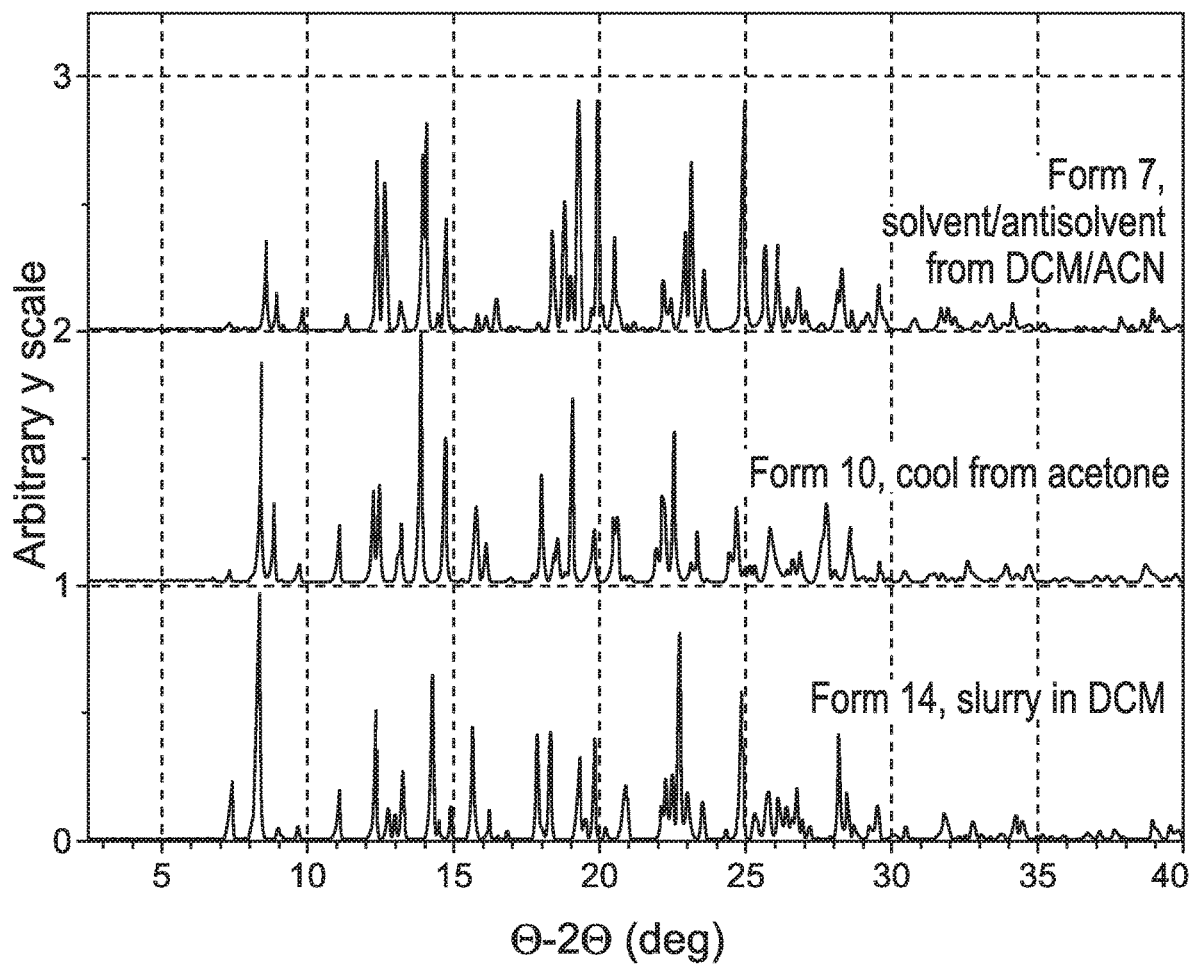
FIG. 9 shows the XRPD spectra of a family of isostructural solvates (Forms 7, 10 and 14) of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

FIG. 9 shows the XRPD spectra for the family of isostructural solvates corresponding to Form 7 (top), Form 10 (middle) and Form 14 (bottom). The XRPD patterns for Forms 7, 10 and 14 were successfully indexed, indicating that the materials were primarily a single crystalline phase. The indexing results had a larger estimated volume per formula unit than expected for an anhydrous form of Compound (I). Form 7 is believed to be an acetonitrile solvate, and indexing results indicates that the free volume could theoretically accommodate approximately 1.75 moles of acetonitrile per mole of Compound I. Form 10 is believed to be an acetone solvate, and indexing results indicates that the free volume could theoretically accommodate approximately 1.5 moles of acetone per mole of Compound I. Form 14 is believed to be a DCM (dichloro methane) solvate, and indexing results indicates that the free volume could theoretically accommodate approximately 1.5 moles of DCM per mole of Compound I. Overlaying peaks shown in FIG. 9 for the family of isostructural solvates are listed in Table 5, with prominent peaks listed in Table 6.

TABLE 5

Overlay of Forms 7, 10 and 14 (isostructural family) XRPD Peaks - Solvates Common 2Θ value

| 8 |
| 12 |
| 14 |
| 19 |
| 21 |
| 23 |
| 25 |
| 26 |
| 28 |

TABLE 6

Overlay of Forms 7, 10 and 14 (isostructural family) Prominent XRPD Peaks - Solvates Common 2Θ value

| 8 |
| 14 |
| 19 |
| 23 |
| 25 |
| 28 |

Disordered Amorphous Forms of Compound (I) Free Base

Figure 10:
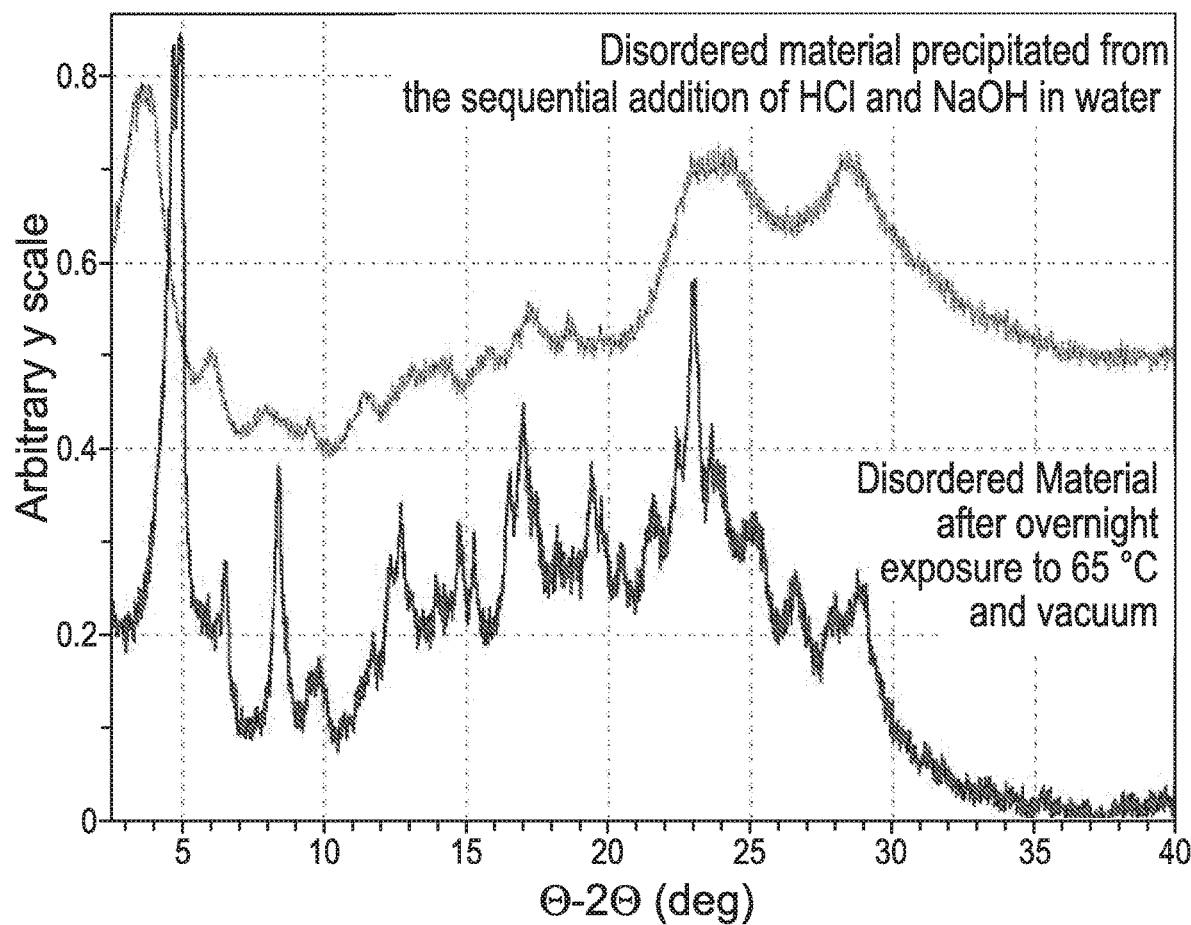
FIG. 10 shows the XRPD spectra of disordered (amorphous) forms of the 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one free base.

FIG. 10 shows the XRPD spectra for amorphous forms (disordered forms) of the Compound (I) free base. The top XRPD spectrum in FIG. 10 corresponds to a disordered (amorphous) material prepared by precipitation from water with the sequential addition of HCl and NaOH. The bottom XRPD spectrum in FIG. 10 corresponds to the same disordered material, following exposure to 65° C. and vacuum overnight. Table 7 below lists peaks shown for the disordered materials.

TABLE 7

Disordered Amorphous Forms XRPD Peaks 2Θ value

| 23 |
| 29 |

Example 3—Crystalline Salt Forms

Method of Analysis
X-Ray Powder Diffraction

XRPD analysis was carried out with a PANalytical X'Pert PRO, scanning the samples between 3 and 35 °2Θ. The plate was loaded inot the PANalytical X'Pert PRO running in transmission mode and analyzed, using a step size of 0.0130 °2Θ, continuous scanning, a divergence slit size of 1.0000°, measurement temperature of 25.00° C., and Cu anode material.

Proton NMR Spectroscopy

Proton NMR Spectroscopy experiments were performed on a Bruker AV500 (frequency: 500 MHz). Experiments were performed in deuterated DMSO and each sample was prepared to about 10 mM concentration.

Hydrochloride Salt Form

A crystalline hydrochloride salt form of Compound I was prepared by placing 300 mg of the free base of Compound I, as prepared by the synthetic method of Example 1, in a 20 mL vial, and dissolving in 4.5 mL of dichloromethane (DCM). Hydrochloric acid was diluted in 1.5 mL DCM and added as a solution, to provide one equivalent of counterion to the solution containing the Compound I. The mixture was then temperature cycled between ambient temperature (~22° C.) and 40° C. in 4 hour cycles for ~72 hours. The sample was left to evaporate ~¼ of its volume and stored at 5° C. for ~24 hours, after which the solid material obtained by salt formation was isolated by filtration using a Millipore 0.45 μm filter membrane, dried under vacuum for ~45 minutes, and analyzed by XRPD and NMR.

Figure 11:
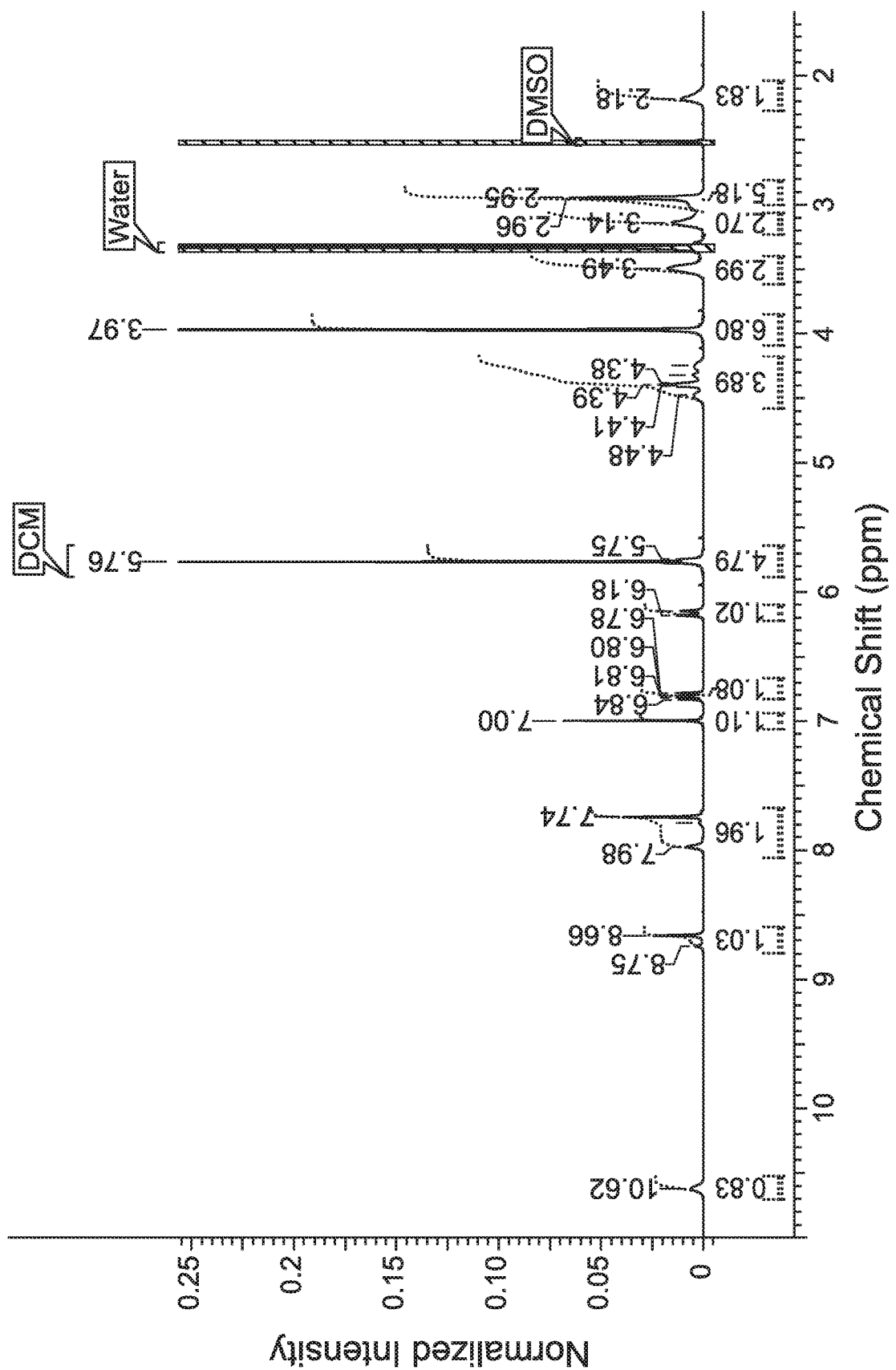
FIG. 11 shows the proton NMR spectrum of a hydrochloride salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one.

FIG. 11 shows the NMR spectrum for the resulting hydrochloride salt. The NMR spectrum showed shifts in signal positions at 5.65 ppm, 4.38 ppm, 3.14 ppm, 2.32 ppm and 1.86 ppm, indicating salt formation. Distinct, well-defined and birefringent columns and prisms were observed by Polarized Light Microscopy (PLM), and the hydrochloride salt was found to be 97.2% pure by High Performance Liquid Chromatography.

Figure 12:
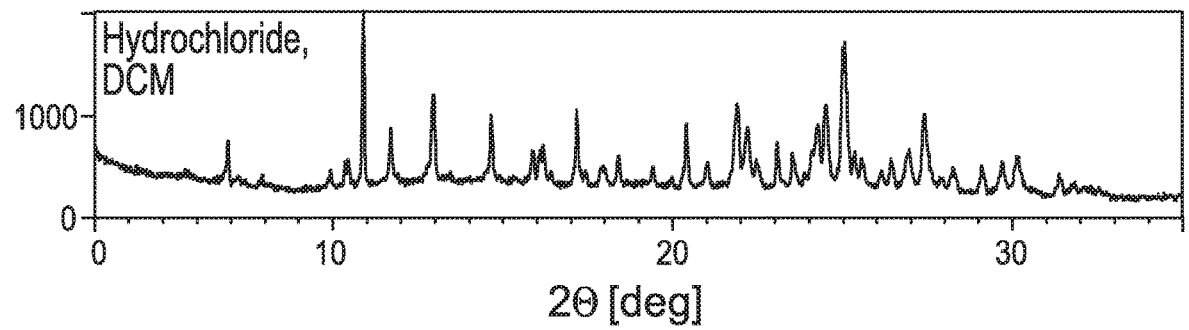
FIG. 12 shows the XRPD spectrum of a crystalline hydrochloride salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one.

FIG. 12 shows the XRPD spectrum for the obtained crystalline hydrochloride salt. Peaks shown in FIG. 12 are listed in Table 8, with prominent peaks listed in Table 9.

TABLE 8

Hydrochloride Salt Form XRPD Peaks

| 2Θ value | Intensity (cts) |
| --- | --- |
| 11 | 2,000 |
| 13 | 1,000 |
| 15 | 800 |

TABLE 8-continued

Hydrochloride Salt Form XRPD Peaks

| 2Θ value | Intensity (cts) |
|---|---|
| 17 | 900 |
| 20 | 700 |
| 22 | 800 |
| 24 | 800 |
| 25 | 12,000 |
| 27 | 600 |

TABLE 9

Hydrochloride Salt Form Prominent XRPD Peaks

| 2Θ value | Intensity (cts) |
|---|---|
| 11 | 2,000 |
| 13 | 1,000 |
| 17 | 900 |
| 25 | 12,000 |

Maleate Salt Form

A crystalline maleate salt form of Compound I was prepared by placing 300 mg of the free base of Compound I, as prepared by the synthetic method of Example 1, in a 20 mL vial, and dissolving in 4.5 mL of dichloromethane (DCM). Maleic acid was added thereto as a slurry in 1.5 mL of DCM, to provide one equivalent of counterion to the solution containing the Compound I. The mixture was then temperature cycled between ambient temperature (~22° C.) and 40° C. in 4 hour cycles for ~72 hours. Solid material obtained by salt formation was isolated by filtration using a Millipore 0.45 μm filter membrane, dried under vacuum for ~45 minutes, and analyzed by XRPD and NMR.

Figure 13:
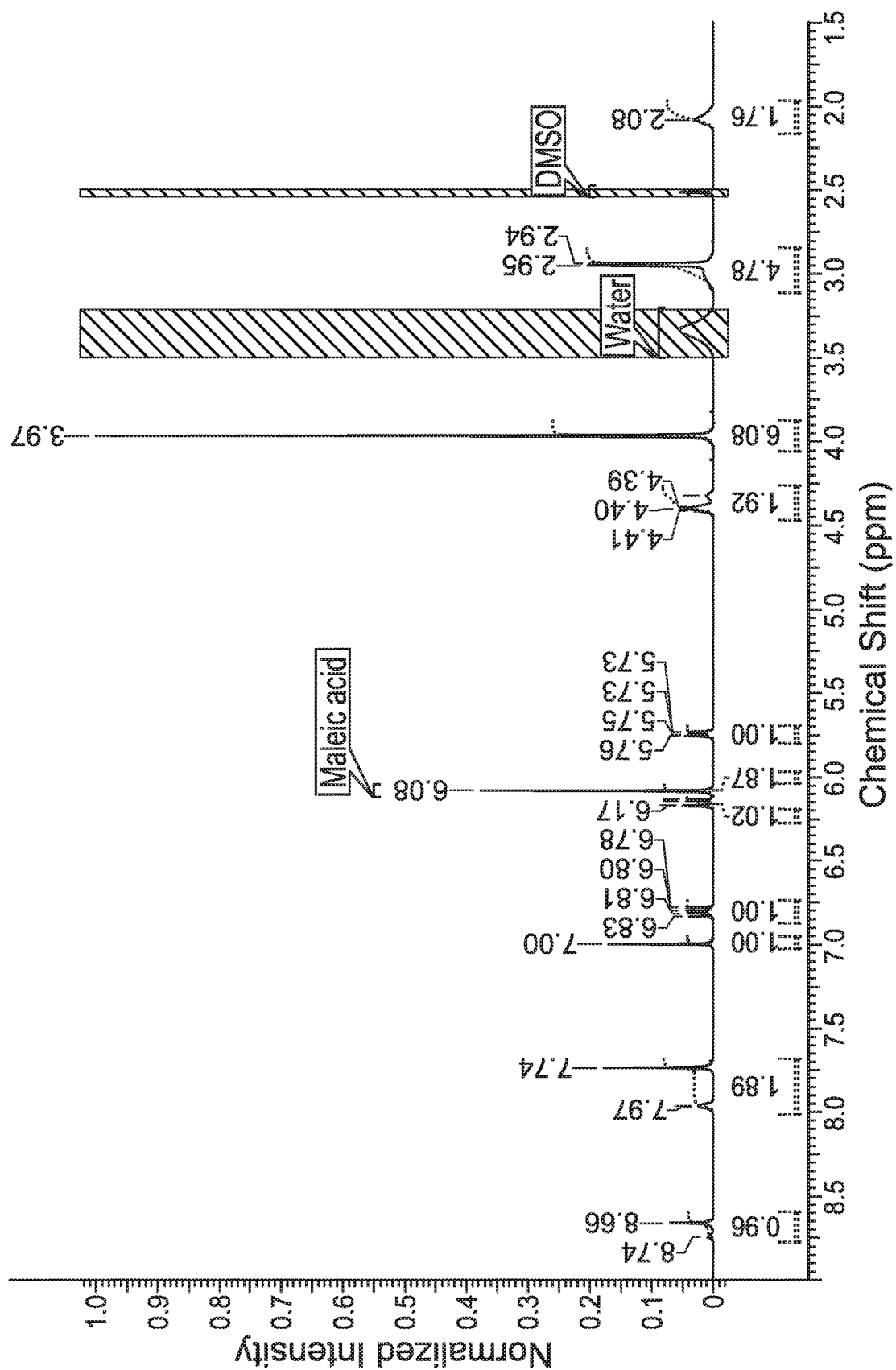
FIG. 13 shows the proton NMR spectrum of a maleate salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one.

FIG. 13 shows the NMR spectrum for the resulting maleate salt. The NMR spectrum showed shifts in signal positions at 3.48 ppm, 2.40 ppm, 2.31 ppm, and 1.85 ppm, indicating salt formation. Birefringent needles and laths were obtained, and the maleate salt was found to be 97.7% pure by High Performance Liquid Chromatography.

Figure 14:
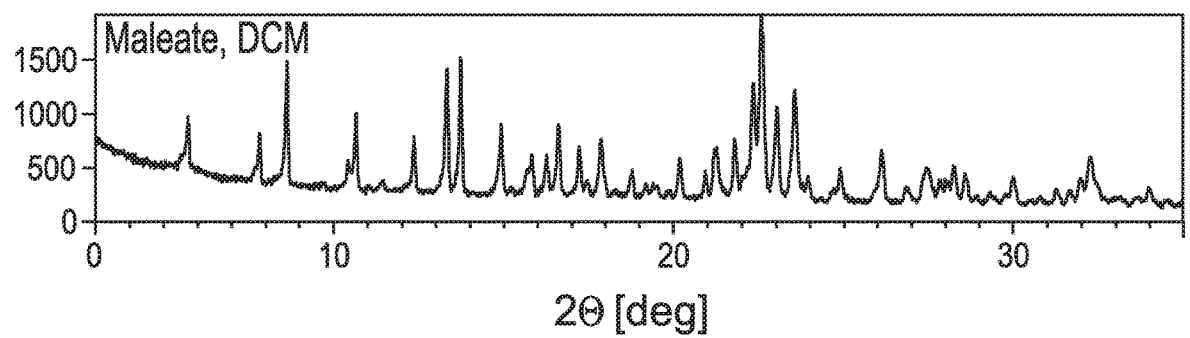
FIG. 14 shows the XRPD spectrum of a crystalline maleate salt of 6-(2,6-dichloro-3,5-dimethoxyphenyl)-2-(methylamino)-8-[3-[4-(prop-2-enoyl)piperazin-1-yl]propyl]-7H,8H-pyrido[2,3-d]pyrimidin-7-one.

FIG. 14 shows the XRPD spectrum for the obtained crystalline maleate salt. Peaks shown in FIG. 14 are listed in Table 10, with prominent peaks listed in Table 11.

TABLE 10

Maleate Salt Form XRPD Peaks

| 2Θ value | Intensity (cts) |
|---|---|
| 8 | 1,200 |
| 10.5 | 800 |
| 13 | 1,100 |
| 13.5 | 1,100 |
| 15 | 1,000 |
| 16.5 | 700 |
| 22 | 1,000 |
| 22.5 | 1,500 |
| 23 | 800 |

TABLE 11

Maleate Salt Form Prominent XRPD Peaks

| 2Θ value | Intensity (cts) |
|---|---|
| 8 | 1,200 |
| 13 | 1,100 |
| 13.5 | 1,100 |
| 22 | 1,000 |
| 22.5 | 1,500 |

CITED REFERENCES

1. The United States Pharmacopeia-National Formulary, The United States Pharmacopeia) Convention, Rockville, Md.

All documents cited in this application are hereby incorporated by reference as if recited in full herein.

What is claimed is:

1. A process of preparing a compound of formula (1):

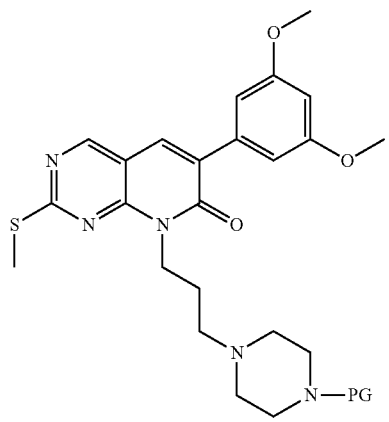

(1)

comprising:

(G) reacting a compound of formula (e):

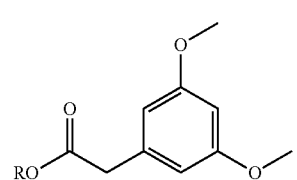

(e)

where R is alkyl; with a compound of formula (f):

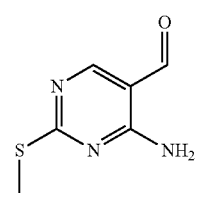

(f)

and (H) treating a compound of formula (g) formed in situ

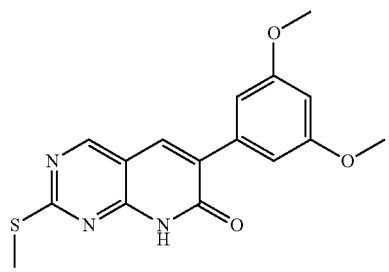
(g)

from the reaction of compound (e) and (f) with a compound of formula (h) or a salt thereof

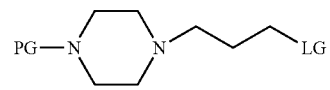
(h)

under alkylating reaction conditions to provide a compound of formula (1), where PG in formula (1) and formula (h) is an amino protecting group.

2. The process of claim 1 wherein Step G is carried out in the presence of a base, and in a polar organic solvent.

3. The process of claim 1 wherein the process of Step H is carried out in the presence of a base and in a polar organic solvent.

4. A process for preparing a compound of formula (2) and/or (3):

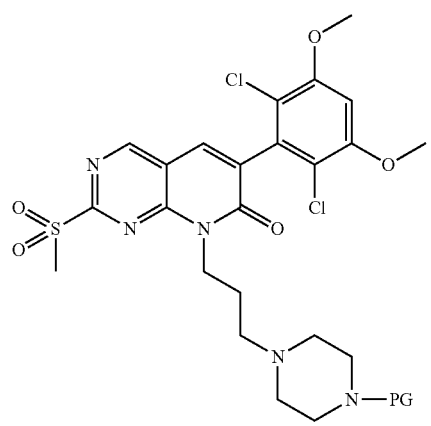
(2)

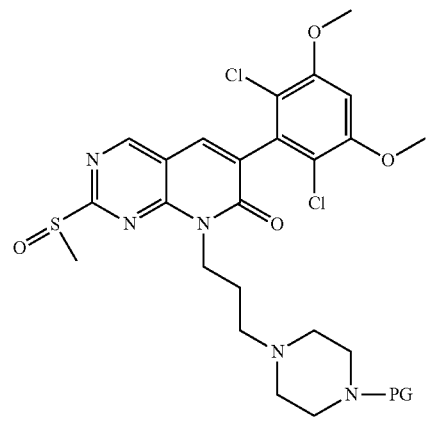
(3)

comprising reacting a compound of formula (1):

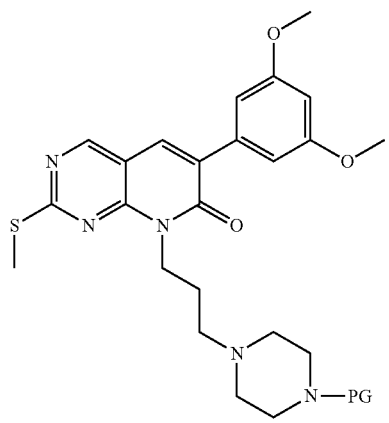
(1)

with a N-chlorosuccinimide (NCS) to provide the compound of formula (2) and/or (3):

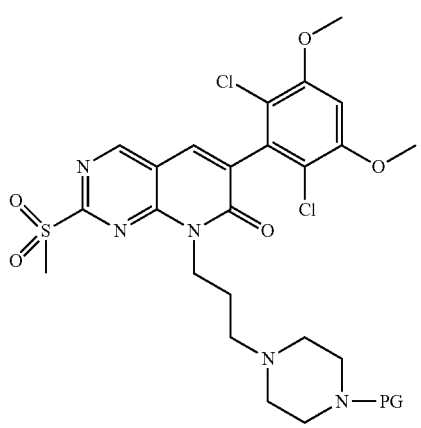
(2)

and/or

-continued
(3)
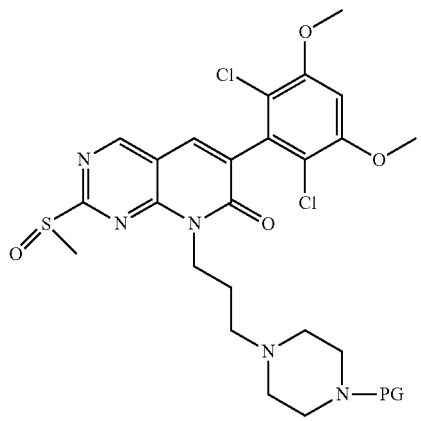
where PG is an amino protecting group.
5. A process for preparing a compound of formula (4):
(4)
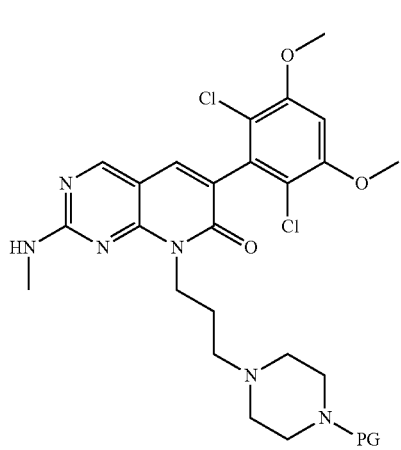
comprising treating a compound of formula (2) and/or (3):
(2)
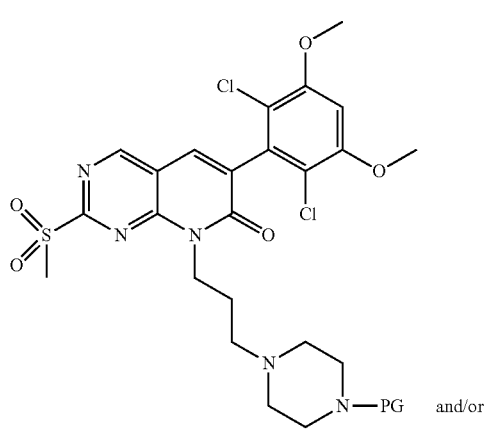
and/or
-continued
(3)
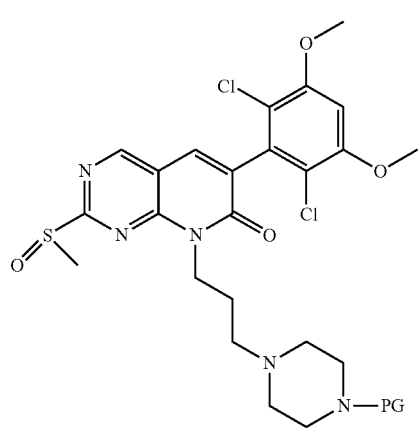
with methylamine to give the compound of formula (4)
(4)
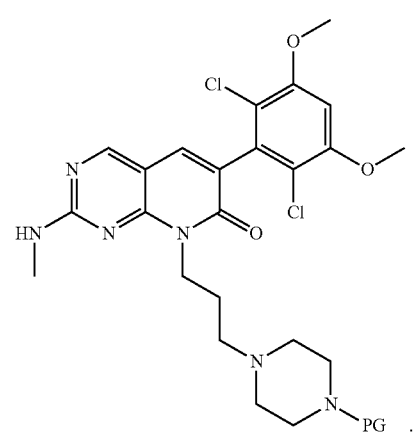
6. A process for preparing a compound of formula (5):
(5)
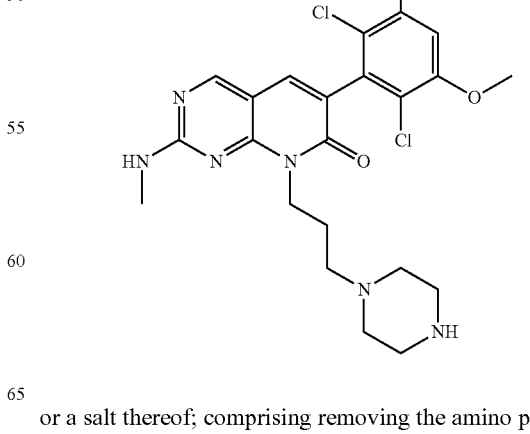
or a salt thereof; comprising removing the amino protecting group "PG" of compound (4)

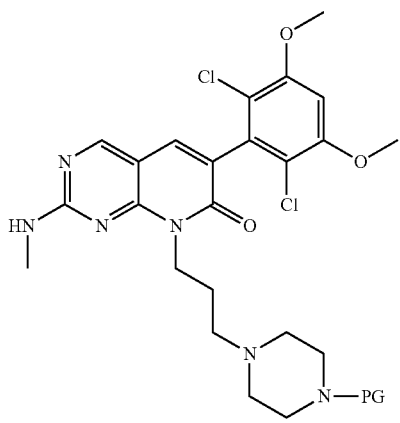

(4)

to give the compound of formula (5):

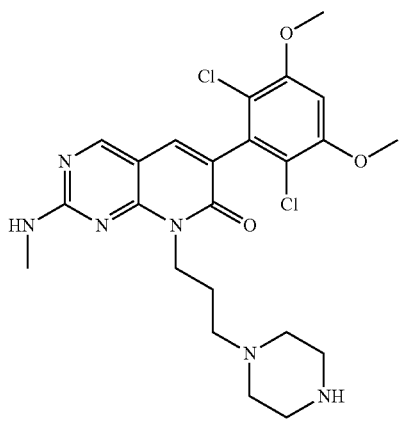

(5)

or a salt thereof.

7. A process of preparing a compound of formula (d) comprising reacting a compound of formula (6) with a compound of formula (iii) where LG is a leaving group under acylating reaction conditions

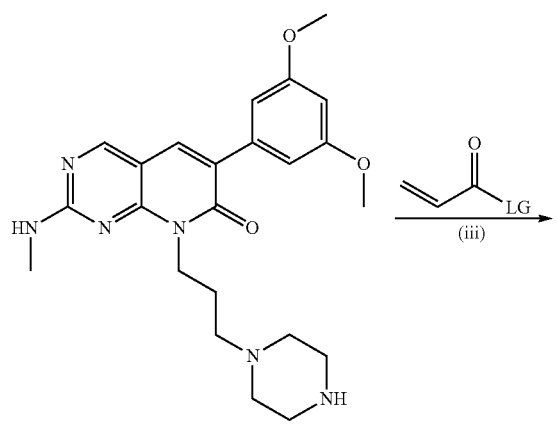

(6)

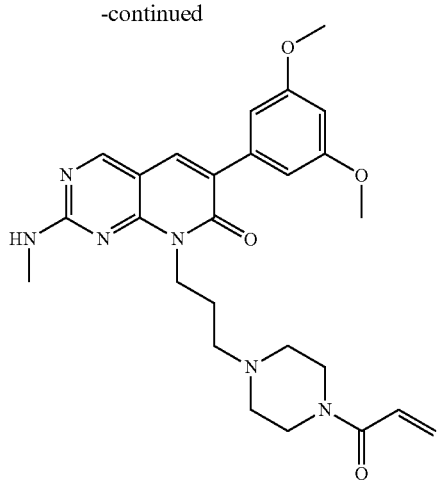

(d)

to give a compound of formula (d); or
reacting a compound of formula (6) with propenoic acid under amide bond formation reaction conditions:

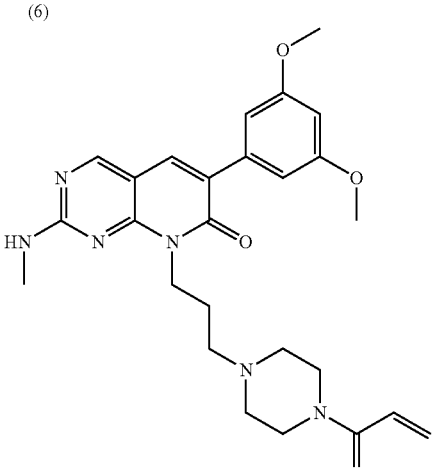

(6)

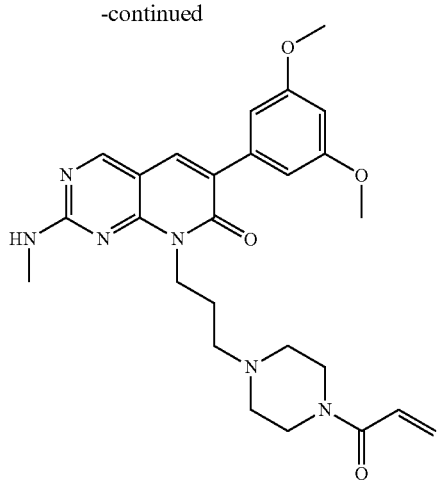

(d)

to give a compound of formula (d).

* * * * *